US008921257B2

(12) United States Patent
Hazin et al.

(10) Patent No.: US 8,921,257 B2
(45) Date of Patent: Dec. 30, 2014

(54) DUAL FUNCTION PARTIAL OXIDATION CATALYST FOR PROPANE TO ACRYLIC ACID CONVERSION

(75) Inventors: Paulette Hazin, Sugar Land, TX (US); Reginald L. Tennyson, Missouri City, TX (US); Michael E. Huckman, Richmond, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 249 days.

(21) Appl. No.: 13/310,693

(22) Filed: Dec. 2, 2011

(65) Prior Publication Data
US 2013/0144085 A1  Jun. 6, 2013

(51) Int. Cl.
*B01J 23/00* (2006.01)
*B01J 27/057* (2006.01)

(52) U.S. Cl.
USPC .......................... 502/313; 502/215; 502/312

(58) Field of Classification Search
USPC .................................. 502/215, 312, 313
See application file for complete search history.

(56) References Cited

U.S. PATENT DOCUMENTS

| 3,907,712 A | 9/1975 | Ohara et al. ............. 502/243 |
| 3,928,462 A | 12/1975 | Shiraishi et al. ......... 568/480 |
| 3,929,899 A | 12/1975 | Grasselli et al. ........ 568/476 |
| 3,933,751 A | 1/1976 | Callahan et al. ......... 568/477 |
| 3,936,505 A | 2/1976 | Oda et al. ............... 502/215 |
| 3,946,081 A | 3/1976 | Wedemeyer et al. .... 568/470 |
| 3,954,856 A | 5/1976 | Kobayashi et al. ...... 562/538 |
| 3,956,181 A | 5/1976 | Grasselli et al. ........ 502/212 |
| 3,956,378 A | 5/1976 | Grasselli et al. ........ 562/546 |
| 3,959,384 A | 5/1976 | Takenaka et al. ........ 568/479 |
| 3,963,645 A | 6/1976 | Gelbein .................... 502/248 |
| 3,966,823 A | 6/1976 | Takenaka et al. ........ 568/479 |
| 3,972,920 A | 8/1976 | Ishii et al. ................ 562/538 |
| 3,980,709 A | 9/1976 | Kubo et al. .............. 568/479 |
| 3,984,477 A | 10/1976 | Kubo et al. .............. 568/479 |
| 3,993,673 A | 11/1976 | McMullen ............... 549/531 |
| 4,001,317 A | 1/1977 | Grasselli et al. ........ 562/546 |
| 4,012,449 A | 3/1977 | Shikakura et al. ....... 568/471 |
| 4,025,565 A | 5/1977 | Oda et al. ................. 568/477 |
| 4,034,008 A | 7/1977 | Kutz et al. ............... 562/546 |
| 4,035,418 A | 7/1977 | Okada et al. ............ 562/538 |
| 4,040,978 A | 8/1977 | Li ............................ 502/212 |
| 4,045,478 A | 8/1977 | Umemura et al. ....... 562/535 |
| 4,049,577 A | 9/1977 | Childress et al. ........ 502/178 |
| 4,052,450 A | 10/1977 | Krabetz et al. .......... 562/546 |
| 4,052,462 A | 10/1977 | Sakakibara et al. ..... 568/477 |
| 4,060,545 A | 11/1977 | Miller et al. ............. 560/208 |
| 4,065,507 A | 12/1977 | Hardman et al. ........ 568/477 |
| 4,066,704 A | 1/1978 | Harris et al. ............. 568/475 |
| 4,078,004 A | 3/1978 | Schlaefer et al. ........ 568/479 |
| 4,087,382 A | 5/1978 | Khoobiar ................. 502/249 |
| 4,111,984 A | 9/1978 | Ishii et al. ................ 562/538 |
| 4,111,985 A | 9/1978 | Okada et al. ............. 562/546 |
| 4,118,419 A | 10/1978 | Ishii et al. ................ 562/534 |
| 4,124,634 A | 11/1978 | Gotoh et al. ............. 562/532 |
| 4,127,603 A | 11/1978 | Bljumberg et al. ...... 562/533 |
| 4,129,600 A | 12/1978 | Childress et al. ........ 568/479 |
| 4,134,859 A | 1/1979 | Kurtz et al. .............. 502/249 |
| 4,148,757 A | 4/1979 | Brazdil et al. ........... 502/205 |
| 4,151,117 A | 4/1979 | Schlaefer ................. 502/212 |
| 4,155,938 A | 5/1979 | Yamamoto et al. ...... 568/479 |
| 4,162,234 A | 7/1979 | Grasselli et al. ......... 502/205 |
| 4,166,808 A | 9/1979 | Daumas et al. .......... 502/249 |
| 4,170,570 A | 10/1979 | Zagata et al. ............ 502/211 |
| 4,171,328 A | 10/1979 | Umemura et al. ....... 568/479 |
| 4,171,454 A | 10/1979 | Miller et al. ............. 562/546 |
| 4,174,354 A | 11/1979 | Grasselli et al. ......... 585/626 |
| 4,174,459 A | 11/1979 | Sakamoto et al. ....... 562/534 |
| 4,176,234 A | 11/1979 | Grasselli et al. ......... 562/546 |
| 4,180,678 A | 12/1979 | Wada et al. .............. 562/534 |
| 4,182,907 A | 1/1980 | Grasselli et al. ......... 562/546 |

(Continued)

FOREIGN PATENT DOCUMENTS

| EP | 0 025 715 B1 | 3/1981 | ............. C07C 27/14 |
| EP | 0 169 449 B1 | 1/1986 | ............. C07C 47/22 |

(Continued)

OTHER PUBLICATIONS

M. Ai, Journal of Catalysis, 101, 389-395 (1986).
Written Opinion of the International Searching Authority for International Application No. PCT/US2012/067422; International Filing Date: Nov. 30, 2012; 10 Pages.
International Search Report of the International Searching Authority for International Application No. PCT/US2012/067422; International Filing Date: Nov. 30, 2012; 5 Pages.

* cited by examiner

*Primary Examiner* — Roy King
*Assistant Examiner* — Jenny Wu
(74) *Attorney, Agent, or Firm* — Cantor Colburn LLP

(57) ABSTRACT

Catalyst compositions including a compound of the following general formula (I):

$$MoV_aNb_bPt_cM_dZ_eO_x \qquad (I)$$

a is a number having a value between about 0.15 and about 0.50,
b is a number having a value between about 0.05 and about 0.30,
c is a number having a value between about 0.0001 and about 0.10,
d is a number having a value between about 0.0 and about 0.35,
e is a number having a value between about 0 and about 0.10,
x is a number depending on the relative amount and valence of the elements different from oxygen in formula (I),
M is one or more elements selected from the group consisting of Ag, Te, and Sb, and
Z is one or more element selected from Ru, Mn, Sc, Ti, Cr, Fe, Co, Ni, Cu, Zn, Ga, Y, Zr, Rh, Pd, In, Ce, Pr, Nd, Sm, Tb, Ta, W, Re, Ir, Au, Pb, B, and mixtures thereof,
where the compositions are capable of simultaneously oxidizing an alkane to a desired product and by-product carbon monoxide to carbon dioxide, with only a minor change in catalyst activity and selectivity.

26 Claims, 17 Drawing Sheets

(56) References Cited

U.S. PATENT DOCUMENTS

| | | | |
|---|---|---|---|
| 4,184,981 A | 1/1980 | Vanderspurt | 502/209 |
| 4,186,152 A | 1/1980 | Yamamoto et al. | 568/477 |
| 4,190,608 A | 2/1980 | Grasselli et al. | 562/546 |
| 4,195,187 A | 3/1980 | Vanderspurt | 562/545 |
| 4,205,181 A | 5/1980 | Murib | 560/241 |
| 4,208,303 A | 6/1980 | Sasaki et al. | 502/38 |
| 4,209,640 A | 6/1980 | Yamamoto et al. | 562/532 |
| 4,212,767 A | 7/1980 | Daniel | 502/211 |
| 4,217,309 A | 8/1980 | Umemura et al. | 568/477 |
| 4,219,670 A | 8/1980 | Okada et al. | 562/546 |
| 4,224,187 A | 9/1980 | Vanderspurt | 502/212 |
| 4,224,193 A | 9/1980 | Vanderspurt | 502/307 |
| 4,225,466 A | 9/1980 | Wada et al. | 502/209 |
| 4,230,639 A | 10/1980 | Khoobiar | 568/471 |
| 4,230,640 A | 10/1980 | Khoobiar | 568/477 |
| 4,240,931 A | 12/1980 | Milberger et al. | 502/306 |
| 4,245,118 A | 1/1981 | Yamamoto et al. | 562/532 |
| 4,248,803 A | 2/1981 | Vanderspurt | 568/477 |
| 4,250,339 A | 2/1981 | Sakamoto et al. | 568/471 |
| 4,252,683 A | 2/1981 | Khoobiar | 502/211 |
| RE30,545 E | 3/1981 | Khoobiar | 502/249 |
| 4,258,217 A | 3/1981 | Aoshima et al. | 568/474 |
| 4,261,858 A | 4/1981 | Khoobiar | 502/211 |
| 4,267,385 A | 5/1981 | Umemura et al. | 568/479 |
| 4,267,386 A | 5/1981 | Vanderspurt | 568/480 |
| 4,271,040 A | 6/1981 | Khoobiar | 502/211 |
| 4,272,408 A | 6/1981 | Daniel | 502/211 |
| 4,272,637 A | 6/1981 | Yamamoto et al. | 568/780 |
| 4,276,196 A | 6/1981 | Dalton et al. | 502/212 |
| 4,280,928 A | 7/1981 | Kirch et al. | 502/205 |
| 4,280,929 A | 7/1981 | Shaw et al. | 502/215 |
| 4,292,203 A | 9/1981 | Milberger et al. | 502/304 |
| 4,297,247 A | 10/1981 | Krabetz et al. | 502/310 |
| 4,298,763 A | 11/1981 | Engelbach et al. | 568/479 |
| 4,303,550 A | 12/1981 | Callahan et al. | 502/24 |
| 4,306,088 A | 12/1981 | Nakamura et al. | 568/471 |
| 4,306,090 A | 12/1981 | Kirch et al. | 568/481 |
| 4,311,611 A | 1/1982 | Sasaki et al. | 502/22 |
| 4,316,856 A | 2/1982 | Guttmann et al. | 558/322 |
| 4,320,227 A | 3/1982 | Matsumoto et al. | 562/534 |
| 4,321,160 A | 3/1982 | Farrington et al. | 502/209 |
| 4,323,703 A | 4/1982 | Grasselli et al. | 562/546 |
| 4,332,971 A | 6/1982 | Dalton et al. | 568/480 |
| 4,337,364 A | 6/1982 | Solomon | 568/475 |
| 4,339,355 A | 7/1982 | Decker et al. | 502/343 |
| 4,341,900 A | 7/1982 | Ishii et al. | 562/532 |
| 4,351,963 A | 9/1982 | Ray et al. | 568/477 |
| 4,354,044 A | 10/1982 | Aoshima et al. | 568/479 |
| 4,356,316 A | 10/1982 | Aoshima et al. | 560/208 |
| RE31,088 E | 11/1982 | Grasselli et al. | 562/535 |
| 4,370,490 A | 1/1983 | Gruber et al. | 560/214 |
| 4,374,759 A | 2/1983 | Khoobiar | 502/249 |
| 4,377,501 A | 3/1983 | Khoobiar | 502/211 |
| 4,380,664 A | 4/1983 | Ishii et al. | 562/546 |
| 4,388,223 A | 6/1983 | Ferlazzo et al. | 502/211 |
| 4,388,225 A | 6/1983 | Solomon | 502/346 |
| 4,397,771 A | 8/1983 | Grasselli et al. | 502/306 |
| 4,400,364 A | 8/1983 | Storm | |
| 4,404,397 A | 9/1983 | Daniel | 562/546 |
| 4,413,147 A | 11/1983 | Khoobiar | 568/476 |
| 4,414,134 A | 11/1983 | Friedrich et al. | 502/204 |
| 4,415,482 A | 11/1983 | Ebner | 502/205 |
| 4,419,270 A | 12/1983 | Ueshima et al. | 502/209 |
| 4,424,141 A | 1/1984 | Grasselli et al. | 502/205 |
| 4,425,255 A | 1/1984 | Toyoda et al. | 502/38 |
| 4,442,308 A | 4/1984 | Arntz et al. | 568/480 |
| 4,443,555 A | 4/1984 | Callahan et al. | 502/211 |
| 4,443,556 A | 4/1984 | Aoki et al. | 502/212 |
| 4,444,906 A | 4/1984 | Callahan et al. | 502/211 |
| 4,444,907 A | 4/1984 | Ohdan et al. | 502/211 |
| 4,446,328 A | 5/1984 | Aoshima et al. | 568/479 |
| 4,453,006 A | 6/1984 | Shaw et al. | 562/545 |
| 4,454,346 A | 6/1984 | Khoobiar | 562/535 |
| 4,467,113 A | 8/1984 | Matsumoto et al. | 562/535 |
| 4,471,061 A | 9/1984 | Shaw et al. | 502/34 |
| 4,471,062 A | 9/1984 | Farrington et al. | 502/34 |
| 4,479,013 A | 10/1984 | Khoobiar | 568/479 |
| 4,489,170 A | 12/1984 | Krabetz et al. | 502/211 |
| 4,499,301 A | 2/1985 | Murib | 562/546 |
| 4,503,247 A | 3/1985 | Khoobair | 562/535 |
| 4,511,671 A | 4/1985 | Saito et al. | 502/242 |
| 4,518,523 A | 5/1985 | Blum et al. | 502/209 |
| 4,528,398 A | 7/1985 | Callahan et al. | 562/534 |
| 4,530,916 A | 7/1985 | Matsumoto et al. | 502/209 |
| 4,532,365 A | 7/1985 | Khoobiar | 568/479 |
| 4,535,188 A | 8/1985 | Khoobiar | 568/479 |
| 4,537,874 A | 8/1985 | Sato et al. | 502/311 |
| 4,537,998 A | 8/1985 | Shum et al. | 568/483 |
| 4,547,588 A | 10/1985 | Khoobiar | 562/535 |
| 4,552,860 A | 11/1985 | Murib | 502/242 |
| 4,556,731 A | 12/1985 | Guttmann et al. | 562/546 |
| 4,558,028 A | 12/1985 | Tsuneki et al. | 502/211 |
| 4,558,029 A | 12/1985 | Paparizos et al. | 502/211 |
| 4,558,154 A | 12/1985 | Shum et al. | 562/537 |
| RE32,082 E | 2/1986 | Khoobiar | 568/476 |
| 4,585,883 A | 4/1986 | Briggs | 556/42 |
| 4,596,784 A | 6/1986 | Kennelly et al. | 502/209 |
| 4,621,155 A | 11/1986 | Ueshima et al. | 562/534 |
| 4,652,673 A | 3/1987 | Matsumoto et al. | 562/535 |
| 4,677,084 A | 6/1987 | Bergna | 502/8 |
| 4,720,575 A | 1/1988 | Gruber | 560/214 |
| 4,732,884 A | 3/1988 | Sarumaru et al. | 502/205 |
| 4,778,930 A | 10/1988 | Grasselli et al. | 568/477 |
| 4,803,190 A | 2/1989 | Sarumaru et al. | 502/205 |
| 4,816,603 A | 3/1989 | Oh-Kita et al. | 562/538 |
| 4,855,275 A | 8/1989 | Suresh et al. | 502/353 |
| 4,871,700 A | 10/1989 | Uchida et al. | 502/51 |
| 4,916,103 A | 4/1990 | Martan et al. | 502/212 |
| 4,925,823 A | 5/1990 | Krabetz et al. | 502/211 |
| 4,946,819 A | 8/1990 | Sasaki et al. | 502/214 |
| 4,954,650 A | 9/1990 | Abe et al. | 562/534 |
| 4,968,846 A | 11/1990 | Kuragano et al. | 568/479 |
| 4,985,592 A | 1/1991 | Ishii et al. | 562/534 |
| 5,017,542 A | 5/1991 | Martan et al. | 502/209 |
| 5,059,573 A | 10/1991 | Sasaki et al. | 502/205 |
| 5,072,052 A | 12/1991 | Boeck et al. | 568/479 |
| 5,081,314 A | 1/1992 | Kissel et al. | 568/479 |
| 5,082,819 A | 1/1992 | Boeck et al. | 502/212 |
| 5,094,990 A | 3/1992 | Sasaki et al. | 502/214 |
| 5,102,847 A | 4/1992 | Yamamoto et al. | 502/209 |
| 5,132,269 A | 7/1992 | Sasaki et al. | 502/205 |
| 5,138,100 A | 8/1992 | Matsuura | 568/474 |
| 5,139,988 A | 8/1992 | Sasaki et al. | 502/206 |
| 5,144,090 A | 9/1992 | Honda et al. | 568/476 |
| 5,153,162 A | 10/1992 | Kurimoto et al. | 502/209 |
| 5,155,262 A | 10/1992 | Etzkorn et al. | 562/532 |
| 5,166,119 A | 11/1992 | Oh-Kita et al. | 502/205 |
| 5,173,468 A | 12/1992 | Boehning et al. | 502/209 |
| 5,183,936 A | 2/1993 | Etzkorn et al. | 562/532 |
| 5,198,578 A | 3/1993 | Etzkorn et al. | 562/532 |
| 5,198,581 A | 3/1993 | Kawajiri et al. | 562/546 |
| 5,206,431 A | 4/1993 | Hashiba et al. | 562/534 |
| 5,208,371 A | 5/1993 | Kuroda et al. | 562/538 |
| 5,218,146 A | 6/1993 | Takata et al. | 562/535 |
| 5,221,653 A | 6/1993 | Jaeger et al. | 502/212 |
| 5,221,767 A | 6/1993 | Boehning et al. | 562/532 |
| 5,225,389 A | 7/1993 | Caillod et al. | 502/205 |
| 5,245,083 A | 9/1993 | Matsuura | 568/479 |
| 5,250,485 A | 10/1993 | Kuroda et al. | 502/159 |
| 5,264,627 A | 11/1993 | Tazaki et al. | 562/599 |
| 5,276,178 A | 1/1994 | Onodera et al. | 562/537 |
| 5,300,707 A | 4/1994 | Caillod et al. | 568/480 |
| 5,349,092 A | 9/1994 | Watanabe et al. | 568/480 |
| 5,364,825 A | 11/1994 | Neumann et al. | 502/311 |
| 5,380,933 A | 1/1995 | Ushikubo et al. | 562/549 |
| 5,491,258 A | 2/1996 | Watanabe et al. | 562/538 |
| 5,532,199 A | 7/1996 | Watanabe et al. | 502/311 |
| 5,602,280 A | 2/1997 | Nagai et al. | 562/546 |
| 5,618,974 A | 4/1997 | Kurimoto et al. | 562/532 |
| 5,670,702 A | 9/1997 | Jackson et al. | 560/208 |
| 5,681,790 A | 10/1997 | Kim et al. | 502/164 |
| 5,684,188 A | 11/1997 | Hefner et al. | 562/532 |
| 5,700,752 A | 12/1997 | Kurimoto et al. | 502/311 |
| 5,728,894 A | 3/1998 | Nagano et al. | 568/479 |

(56) References Cited

U.S. PATENT DOCUMENTS

| | | | |
|---|---|---|---|
| 5,739,391 A | 4/1998 | Ruppel et al. | 562/532 |
| 5,817,865 A | 10/1998 | Machhammer et al. | 560/208 |
| 5,821,390 A | 10/1998 | Ruppel et al. | 568/470 |
| 5,856,259 A | 1/1999 | Watanabe et al. | 502/305 |
| 5,877,108 A | 3/1999 | Suresh et al. | 502/20 |
| 5,892,108 A | 4/1999 | Shiotani et al. | 562/532 |
| 5,929,275 A | 7/1999 | Wada et al. | 562/545 |
| 5,948,683 A | 9/1999 | Koermer et al. | 436/37 |
| 5,981,804 A | 11/1999 | Kurimoto et al. | 568/479 |
| 5,990,348 A | 11/1999 | Lyon et al. | 562/549 |
| 6,028,220 A | 2/2000 | Wada et al. | 562/546 |
| 6,043,184 A | 3/2000 | Karmakar et al. | 502/208 |
| 6,060,419 A | 5/2000 | Wijesekera et al. | 502/208 |
| 6,069,271 A | 5/2000 | Tanimoto et al. | 562/545 |
| 6,143,928 A | 11/2000 | Karim et al. | |
| 6,171,571 B1 | 1/2001 | Bedard et al. | 423/594.7 |
| 6,180,825 B1 * | 1/2001 | Lin et al. | 562/549 |
| 6,194,610 B1 * | 2/2001 | Borchert et al. | 562/548 |
| 6,646,158 B1 | 11/2003 | Karim et al. | |
| 6,710,207 B2 | 3/2004 | Bogan, Jr. et al. | |
| 2003/0135071 A1 * | 7/2003 | Hazin et al. | 562/547 |
| 2004/0192966 A1 * | 9/2004 | Hazin et al. | 562/547 |
| 2004/0249204 A1 * | 12/2004 | Ellis | 562/549 |
| 2006/0293539 A1 | 12/2006 | Holtcamp et al. | |

FOREIGN PATENT DOCUMENTS

| | | | |
|---|---|---|---|
| EP | 0 223 877 B1 | 6/1987 | B01J 23/88 |
| EP | 0 267 556 B1 | 5/1988 | B01J 23/88 |
| EP | 0 279 374 B1 | 8/1988 | B01J 23/88 |
| EP | 0 456 837 A1 | 6/1991 | B01J 8/06 |
| EP | 0 450 596 B1 | 10/1991 | B01J 23/88 |
| EP | 0 460 932 B1 | 12/1991 | B01J 23/88 |
| EP | 0 501 794 B1 | 9/1992 | B01J 23/887 |
| EP | 0 523 727 B1 | 1/1993 | B01J 23/88 |
| EP | 0 558 028 B1 | 9/1993 | B01J 23/88 |
| EP | 0 563 025 A1 | 9/1993 | B01J 23/881 |
| EP | 0 574 895 A1 | 12/1993 | B01J 23/88 |
| EP | 0 630 879 A1 | 12/1994 | B01J 23/887 |
| EP | 0 685 260 A2 | 12/1995 | B01J 23/887 |
| EP | 0 767 161 A1 | 4/1997 | C07C 45/35 |
| EP | 1930074 | 11/2008 | |
| EP | 2179793 A1 | 4/2010 | |
| WO | 2006/008177 A1 | 1/2006 | |

DUAL FUNCTION PARTIAL OXIDATION CATALYST FOR PROPANE TO ACRYLIC ACID CONVERSION

BACKGROUND OF THE INVENTION

1. Field of the Invention

Embodiments of this invention relate to dual function catalyst compositions for the partial oxidation of alkanes and the simultaneous oxidation of incompletely oxidized carbon oxides and methods for making and using same.

More particularly, embodiments of this invention relate to dual function catalyst compositions for the partial oxidation of alkanes and the simultaneous oxidation of partially oxidized carbon oxides, where the catalyst compositions include at least one compound of the general formula (I):

$$MoV_aNb_bPt_cM_dZ_eO_x \quad (I)$$

where:
- a is a number having a value between about 0.15 and about 0.50,
- b is a number having a value between about 0.05 and about 0.30,
- c is a number having a value between about 0.0001 and about 0.10,
- d is a number having a value between about 0.0 and about 0.40,
- e is a number having a value between about 0.0 and about 0.10,
- x is a number depending on the relative amount and valence of the elements different from oxygen in formula (I),
- M is one or more of the following elements: Ag, Te, and Sb, and
- Z is one or more element selected from Ru, Mn, Sc, Ti, Cr, Fe, Co, Ni, Cu, Zn, Ga, Y, Zr, Rh, Pd, In, Ce, Pr, Nd, Sm, Tb, Ta, W, Re, Ir, Au, Pb, B, and mixtures thereof.

2. Description of the Related Art

Hydrocarbon conversion reactions are useful industrial processes to convert abundant components of a petroleum feedstock into other compounds having greater industrial utility. Examples of such reactions include the conversion of ethane to ethylene, the conversion of propane to propylene, the conversion of propylene to acrylic acid (AA), the conversion of isobutene to methacrylic acid, the conversion of hexenes to aromatics, or other similar reactions that convert a lower value feedstock into a higher value product. A specific example is the production of acrylic acid from hydrocarbon feedstocks.

Acrylic acid is an important industrial chemical. The global demand for acrylic acid in 2009 was close to 4 million tons per year. The major commercial process to produce acrylic acid is the two-stage oxidation of propylene. In the first stage, propylene is oxidized in the presence of oxygen and steam to acrolein. In the second stage, acrolein is oxidized in the presence of oxygen and steam to acrylic acid. Each stage operates at different optimum temperature and hydrocarbon concentration. Acrylic acid is an important material for the production of many useful products. Acrylic acid undergoes the typical reactions of carboxylic acids, for example esterification with alcohols. The esters and salts of acrylic acid are collectively known as acrylates (or propionates). The most common alkyl esters of acrylic acid are methyl-, butyl-, ethyl-, and 2-ethylhexyl-acrylate. Polymerization of the acids and acrylates results in the commercially important polyacids, polyacrylates and polyalkylacrylates.

Virtually all of the commercially produced acrylic acid is made from the oxidation of propylene. However, oxidation of propane to acrylic acid would be more economical, because propane is a cheaper feedstock than propylene.

Direct propane oxidation to acrylic acid has been investigated for more than two decades as an alternative to the current commercial propylene oxidation process to produce acrylic acid. See, e.g., M. Ai, *Journal of Catalysis,* 101, 389-395 (1986), and U.S. Pat. No. 5,380,933. So far, propane to acrylic acid has not been commercially realized despite the relative price advantage of the propane feedstock.

In the propane oxidation to acrylic acid, it is often advantageous to operate the process such that propane conversion is limited by the available oxygen. The oxygen concentration is controlled at low concentrations to ensure the feed mixture is below the flammability limit of the reaction mixture; however, limiting the available oxygen results in a limited conversion of propane. For the process to be economical, the unreacted propane must then be recovered and recycled. Also, propylene is produced as an intermediate and is recycled along with propane.

Some of the better performing catalysts for oxidizing propane to acrylic acid (AA) produce carbon monoxide (CO) as a significant byproduct, but the catalysts will not further oxidize CO to carbon dioxide ($CO_2$). EP1930074A1 disclosed propane oxidation catalysts according to the formula (I):

$$MoV_aTe_bNb_cZ_dO_x \quad (I)$$

wherein a=0.0-0.50, b=0.0-0.45, c=0-0.5, d≤0.05, and x is a number depending on the relative amount and valence of the elements different from oxygen in formula (I), and Z is at least one element selected from Ru, Mn, Sc, Ti, Cr, Fe, Co, Ni, Cu, Zn, Ga, Y, Zr, Rh, Pd, In, Sb, Ce, Pr, Nd, Te, Sm, Tb, Ta, W, Re, Ir, Pt, Au, Pb, and Bi, provided that at least two different metal species are contained in the catalyst composition, that is, one of a, b, c, and d are not zero.

For reasons of efficiency, high yields of product from starting hydrocarbon material is desirable. One way to improve yield is to recycle unreacted and partially reacted starting material back to the reactor. In propane oxidation to acrylic acid, the unreacted and partially reacted starting materials are propane and propylene. However, the effluent stream also contains the byproduct gases carbon monoxide (CO) and carbon dioxide ($CO_2$). With each pass, CO and $CO_2$ accumulate in the recycle stream to the point at which they reach levels deleterious to the reaction. For this reason, it is important to remove CO and $CO_2$ or otherwise prevent their accumulation in the recycle stream. There are standard processes to remove $CO_2$ from the recycle stream, which are well characterized and relatively inexpensive. For example, $CO_2$ can be scrubbed from the recycle stream by base washing. However, the removal of CO is somewhat more difficult and problematic, and as a result, more costly.

EP2179793 disclosed propane oxidation catalysts according the general formula (I):

$$MoV_aX_bQ_cZ_dO_e \quad (I)$$

wherein X is P, which may be replaced in part by Bi, for instance up to a molar ratio Bi/P of 1/1, Q is at least one of Nb, Ta and W (which includes the combined use of Nb and Ta, Nb and W, and Ta and W, as well as the use of all three elements), a=0.15-0.50, b=0.02-0.45, in particular 0.05-0.40, c=0.05-0.45, d ≤ 0.05 and e is the molar number of oxygen binding to the metal atoms present in this mixed oxide which follows from the relative amount and valence of the metals elements, and Z is at least one element selected from Na, K, Si, Ru, Mn, Sc, Ti, Cr, Fe, Co, Ni, Cu, Zn, Ga, Y, Zr, Rh, Pd, In, Ce, Pr, Nd, Sm, Tb, Re, Ir, Pt, Au, and Pb.

WO2006008177 disclosed metal oxide catalysts comprising the metal oxides of Mo, V, Te and Nb, and may optionally contain oxides of other metal elements, as long as these do not adversely affect the function of the resulting material as a catalyst in the oxidation reactions referred to herein. The calcined catalyst material to be leached in the method of the present invention is a material of the average general formula (I):

$$MoV_aTe_bNb_cZ_dO_x \quad (I)$$

wherein a=0.15-0.50, b=0.10-0.45, in particular 0.10-0.40, c 0.05-0.20, d 0.05 and x is a number depending on the relative amount and valence of the elements different from oxygen in formula (I), and Z is at least one element selected from Ru, Mn, Sc, Ti, Cr, Fe, Co, Ni, Cu, Zn, Ga, Y, Zr, Rh, Pd, In, Sb, Ce, Pr, Nd, Te, Sm, Tb, Ta, W, Re, Ir, Pt, Au, Pb, and Bi.

As CO levels increase in the recycle stream, the recycle stream must be purged to reduce CO levels, but these results in concurrent loss of propane and propylene reducing process efficiency as raw material is lost.

The problem of the accumulation of CO in the recycle stream can be addressed in one of two ways. CO can be removed from recycle stream. As discussed previously, this way is costly and difficult. Alternatively, CO production can be suppressed, prevented or eliminated so that CO accumulation in the recycle stream is prevented, suppressed or eliminated in the first instance.

Thus, it would be beneficial for hydrocarbon conversion processes generally, and specifically for the conversion of propane to acrylic acid, to have a means to minimize or eliminate CO accumulation in the recycle stream. The present invention focuses on the second route to CO mitigation and is directed to the preparation of dual function catalysts that combine propane oxidation to acrylic acid functionality with a mild oxidation functionality to convert CO to $CO_2$, which is more easily removed from the recycle stream. The catalyst of the present invention accomplishes this without detrimentally affecting the propane to acrylic acid functionality.

SUMMARY OF THE INVENTION

Catalysts

Embodiments of this invention provide metal oxide catalyst compositions for the partial oxidation of alkanes comprising oxides of Mo, V, Nb, a relatively small amount of Pt, within a specific range, optionally one or more metal oxides selected from the group consisting of Ag, Te and Sb, and optionally oxides of other metal elements, as long as these other metal oxides do not adversely affect the function of the resulting catalyst compositions in the partial oxidation of the alkanes, where the relatively small and specific amount of Pt is sufficient to render the catalyst compositions capable of simultaneously oxidizing carbon monoxide to carbon dioxide, with only a modest reduction in catalyst activity and selectivity. However, the small reduction in catalyst activity and selectivity is more than offset by the capability of the catalyst compositions of this invention to simultaneously partially oxide the alkanes and co-oxidize CO, reducing purging and the cost of CO destruction during purging. In certain embodiments, the amount of platinum in the catalyst is less than or equal to about 5 wt. %. In other embodiments, the amount of platinum in the catalyst is less than or equal to about 2.5 wt. %. In other embodiments, the amount of platinum in the catalyst is less than or equal to about 1.0 wt. %. In other embodiments, the amount of platinum in the catalyst is less than or equal to about 0.8 wt. %. In other embodiments, the amount of platinum in the catalyst is less than or equal to about 0.6 wt. %. In other embodiments, the amount of platinum in the catalyst is less than or equal to about 0.5 wt. %. In other embodiments, the amount of platinum in the catalyst is less than or equal to about 0.4 wt. %. In other embodiments, the amount of platinum in the catalyst is less than or equal to about 0.3 wt. %. Generally, the pre-catalyst compositions are calcined to form active catalyst compositions. In certain embodiments, the active catalysts may be leached to form leached catalyst compositions.

In certain embodiments, the catalyst compositions of this invention for the partial oxidation of alkanes include at least one compound of the general formula (I):

$$MoV_aNb_bPt_cM_dZ_eO_x \quad (I)$$

where:
  a is a number having a value between about 0.15 and about 0.50, alternatively, a has value between 0.15 and 0.50,
  b is a number having a value between about 0.05 and about 0.30, alternatively, b has value between 0.05 and 0.30,
  c is a number having a value between about 0.0001 and about 0.10, alternatively, c has a value between 0.0001 and 0.10,
  d is a number having a value between about 0.0 and about 0.40, alternatively, d has a value between 0.0 and 0.40,
  e is a number having a value between about 0.0 and about 0.10, alternatively, e has a value between 0.0 and 0.10,
  x is a number depending on the relative amount and valence of the elements different from oxygen in formula (I), and
  M is one or more of the following elements: Ag, Te, and Sb, and
  Z is one or more element selected from Ru, Mn, Sc, Ti, Cr, Fe, Co, Ni, Cu, Zn, Ga, Y, Zr, Rh, Pd, In, Ce, Pr, Nd, Sm, Tb, Ta, W, Re, Ir, Au, Pb, B, and mixtures thereof.

In other embodiments, c is a number having a value between about 0.0001 and about 0.05. In other embodiments, c is a number having a value between about 0.0001 and about 0.03. In other embodiments, c is a number having a value between about 0.0001 and about 0.01. In other embodiments, the compound has platinum at a level between about 0.1 wt. % to about 4.5 wt. %. In other embodiments, the compound has platinum at a level between about 0.1 to about 1.2 wt. %. In other embodiments, the compound has platinum at a level between about 0.1 to about 0.6 wt. %. In other embodiments, the compound has platinum at a level between about 0.1 to about 0.3 wt. %.

In other embodiments, c is a number having a value between 0.0001 and 0.05. In other embodiments, c is a number having a value between 0.0001 and 0.03. In other embodiments, c is a number having a value between 0.0001 and 0.01. In other embodiments, the compound has platinum at a level between 0.1 wt. % to 4.5 wt. %. In other embodiments, the compound has platinum at a level between 0.1 to 1.2 wt. %. In other embodiments, the compound has platinum at a level between 0.1 to 0.6 wt. %. In other embodiments, the compound has platinum at a level between 0.1 to 0.3 wt. %.

In other embodiments, the catalyst compositions of this invention for the partial oxidation of alkanes include at least one compound of the general formula (II):

$$MoV_aNb_bPt_cSb_{d1}Te_{d2}Z_eO_x \quad (II)$$

where:
  a is a number having a value between about 0.15 and about 0.50, alternatively, a has value between 0.15 and 0.50,
  b is a number having a value between about 0.05 and about 0.30, alternatively, b has value between 0.05 and 0.30, c is a number corresponding to an amount of Pt sufficient to reduce a concentration of CO formed in the partial oxidation of the alkanes, d1 is a number having a value between about 0.01 and about 0.40, alternatively, d1 has a value between 0.0 and 0.40, d2 is a number having a value between about 0.01 and about 0.40, alternatively, d2 has a value between 0.0 and 0.40, e is a number having a value between about 0.0 and about 0.10, alternatively, e has a value between 0.0 and 0.10, x is a number depending on the relative amount and valence of the elements different from oxygen in formula (I), and Z is at least one element selected from Ru, Mn, Sc, Ti, Cr, Fe, Co, Ni, Cu, Zn, Ga, Y, Zr, Rh, Pd, In, Sb, Ce, Pr, Nd, Te, Sm, Tb, Ta, W, Re, Ir, Au, Pb, B, and mixtures thereof.

In certain embodiments, the catalyst compositions of this invention including at least one compound of the general formula (III):

$$MoV_aNb_bPt_cSb_{d1}Te_{d2}Z_eO_x \qquad (III)$$

where:
a is a number having a value between about 0.15 and about 0.50, alternatively, a has value between 0.15 and 0.50, b is a number having a value between about 0.05 and about 0.30, alternatively, b has value between 0.05 and 0.30, c is a number having a value between about 0.0001 and about 0.10, alternatively, c has a value between 0.0001 and 0.10, d1 is a number having a value between about 0.01 and about 0.30, alternatively, d1 has a value between 0.0 and 0.30, d2 is a number having a value between about 0.01 and about 0.30, alternatively, d2 has a value between 0.0 and 0.30, e is a number having a value between about 0.0 and about 0.10, alternatively, e has a value between 0.0 and 0.10, x is a number depending on the relative amount and valence of the elements different from oxygen in formula (I), and Z is at least one element selected from Ru, Mn, Sc, Ti, Cr, Fe, Co, Ni, Cu, Zn, Ga, Y, Zr, Rh, Pd, In, Sb, Ce, Pr, Nd, Te, Sm, Tb, Ta, W, Re, Ir, Au, Pb, B, and mixtures thereof.

In certain embodiments, the catalyst compositions of this invention including at least one compound of the general formula (IV):

$$MoV_aNb_bPt_cSb_{d1}Te_{d2}Z_eO_x \qquad (IV)$$

where:
a is a number having a value between about 0.20 and about 0.40, alternatively, a has value between 0.20 and 0.40, b is a number having a value between about 0.10 and about 0.20, alternatively, b has value between 0.10 and 0.20, c is a number having a value between about 0.001 and about 0.075, alternatively, c has a value between 0.001 and 0.075, d1 is a number having a value between about 0.02 and about 0.20, alternatively, d1 has a value between 0.0 and 0.20, d2 is a number having a value between about 0.02 and about 0.20, alternatively, d2 has a value between 0.0 and 0.20, e is a number having a value between about 0.0 and about 0.05, alternatively, e has a value between 0.0 and 0.05, x is a number depending on the relative amount and valence of the elements different from oxygen in formula (I), and Z is at least one element selected from Ru, Mn, Sc, Ti, Cr, Fe, Co, Ni, Cu, Zn, Ga, Y, Zr, Rh, Pd, In, Sb, Ce, Pr, Nd, Te, Sm, Tb, Ta, W, Re, Ir, Au, Pb, B, and mixtures thereof.

In certain embodiments, the catalyst compositions of this invention including at least one compound of the general formula (V):

$$MoV_aNb_bPt_cSb_{d1}Te_{d2}Z_eO_x \qquad (V)$$

where:
a is a number having a value between about 0.25 and about 0.35, alternatively, a has value between 0.25 and 0.35, b is a number having a value between about 0.10 and about 0.15, alternatively, b has value between 0.10 and 0.15, c is a number having a value between about 0.001 and about 0.05, alternatively, c has a value between 0.001 and 0.05, d1 is a number having a value between about 0.04 and about 0.12, alternatively, d1 has a value between 0.04 and 0.12, d2 is a number having a value between about 0.04 and about 0.12, alternatively, d2 has a value between 0.04 and 0.12, e is a number having a value between about 0.0 and about 0.05, alternatively, e has a value between 0.0 and 0.05, x is a number depending on the relative amount and valence of the elements different from oxygen in formula (I), and Z is at least one element selected from Ru, Mn, Sc, Ti, Cr, Fe, Co, Ni, Cu, Zn, Ga, Y, Zr, Rh, Pd, In, Sb, Ce, Pr, Nd, Te, Sm, Tb, Ta, W, Re, Ir, Au, Pb, B, and mixtures thereof.

In certain embodiments, the catalyst compositions of this invention including at least one compound of the general formula (VI):

$$MoV_aNb_bPt_cSb_{d1}Te_{d2}Z_eO_x \qquad (VI)$$

where:
a is a number having a value between about 0.25 and about 0.35, alternatively, a has value between 0.25 and 0.35, b is a number having a value between about 0.10 and about 0.15, alternatively, b has value between 0.10 and 0.15, c is a number having a value between about 0.001 and about 0.05, alternatively, c has a value between 0.001 and 0.05, d1 is a number having a value between about 0.06 and about 0.12, alternatively, d1 has a value between 0.06 and 0.12, d2 is a number having a value between about 0.06 and about 0.12, alternatively, d2 has a value between 0.06 and 0.12, e is a number having a value between about 0.0 and about 0.05, alternatively, e has a value between 0.0 and 0.05, x is a number depending on the relative amount and valence of the elements different from oxygen in formula (I), and Z is at least one element selected from Ru, Mn, Sc, Ti, Cr, Fe, Co, Ni, Cu, Zn, Ga, Y, Zr, Rh, Pd, In, Sb, Ce, Pr, Nd, Te, Sm, Tb, Ta, W, Re, Ir, Au, Pb, B, and mixtures thereof.

In certain embodiments, the catalyst compositions of this invention including at least one compound of the general formula (VII):

$$MoV_aNb_bPt_cSb_{d1}Te_{d2}Z_eO_x \qquad (VII)$$

where:
a is a number having a value between about 0.25 and about 0.35, alternatively, a has value between 0.15 and 0.50, b is a number having a value between about 0.10 and about 0.15, alternatively, b has value between 0.10 and 0.15, c is a number having a value between about 0.001 and about 0.05, alternatively, c has a value between 0.0001 and 0.10, d1 is a number having a value between about 0.06 and about 0.12, alternatively, d1 has a value between 0.06 and 0.12, d2 is a number having a value between about 0.06 and about 0.12, alternatively, d2 has a value between 0.06 and 0.12, e is a number having a value between about 0.0 and about 0.05, alternatively, e has a value between 0.0 and 0.05, x is a number depending on the relative amount and valence of the elements different from oxygen in formula (I), and Z is at least one element selected from Ru, Mn, Sc, Ti, Cr, Fe, Co, Ni, Cu, Zn, Ga, Y, Zr, Rh, Pd, In, Sb, Ce, Pr, Nd, Te, Sm, Tb, Ta, W, Re, Ir, Au, Pb, B, and mixtures thereof.

It should be understood in the formulas (I-VII) that if the compounds have more than one M elements or more than one Z elements, then amount of each M element in the compound can vary within the specified range of d and each Z elements can vary within specified range of e. Thus, in the compounds of formulas II-VII, the values of d1 and d2 may independently range between the specified values and do not have to sum to d of the compounds of formula I.

Methods for Making

Embodiments of this invention provide methods for making a catalyst of this invention comprising the step of preparing a first mixture of Mo, V, Te, Sb and Pt in water added in order with stirring and heating. The resulting mixture is then stirred at an elevated temperature for a heating time and then cooled to cooled temperature. The methods also include preparing a second mixture including oxalic acid and Nb in water with stirring and heating to a second heating temperature and a second heating time. The second mixture is then cooled to a second cooling temperature. The second mixture is then added to the first mixture and spray dried to form a catalyst precursor. The catalyst precursor is then air dried at a drying temperature for a drying time. The catalyst precursor is then decomposed at a decomposing temperature for a decomposing time. The decomposed catalyst precursor is then calcined at a calcining temperature for a calcining time to form an active catalyst. The active catalyst is then ground and sieved to a 18/35 mesh size.

Methods for Making

Embodiments of this invention provide methods for using a catalyst of this invention comprising the step of contacting an alkane with oxygen in the presence of a catalyst of this invention under alkane oxidation conditions in a reactor to produce a desired alkane oxidation product and to concurrently reduce a concentration of co-produced carbon monoxide (CO). The alkane oxidation product is then recovered. The methods of this invention also include recycling an effluent stream, where the catalyst reduces the amount of CO in the recycle stream. The methods also include minimizing purges due to the build up of CO reducing hydrocarbon loss and improving the overall performance of the method. In certain embodiments, the alkane is propane and the desired product is acrylic acid. In other embodiments, the alkane is isobutane and the product is methacrylic acid. In other embodiments, the alkane is n-butane and the product is 2-methyl-acrylic acid. In other embodiments, the alkane is 2-methylpentane and the product is 2-methyl-methacrylic acid. In other embodiments, the alkane is n-pentane and the product is 2-ethyl-acrylic acid.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
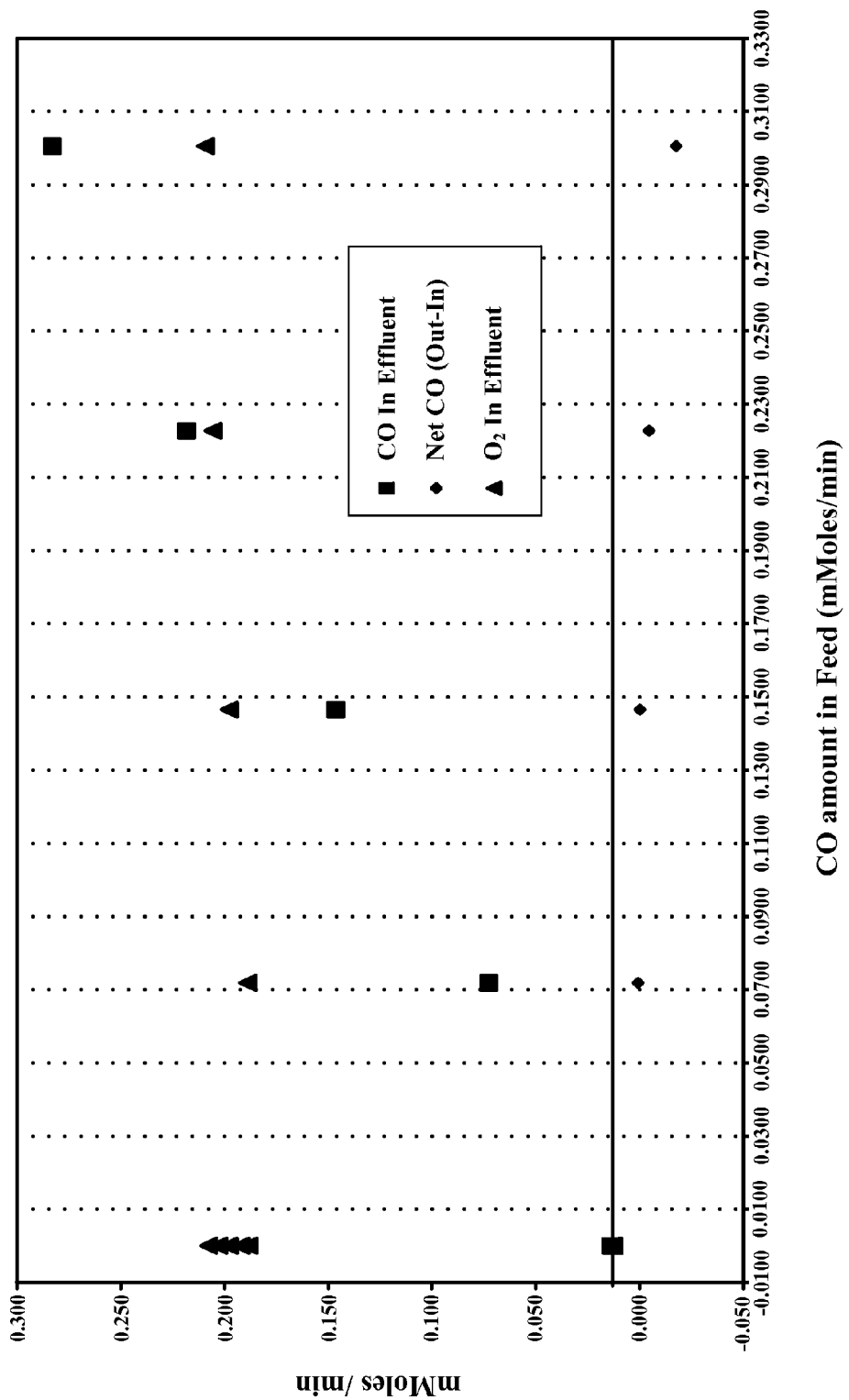
FIG. 1 depicts CO oxidation performance of Catalyst 1.

The inventors have found that a standard alkane partial oxidation catalyst can be rendered dual functional by the addition of an amount of an auxiliary metal sufficient to convert the standard propane partial oxidation catalyst into a dual function catalyst capable of simultaneously partially oxidizing an alkane to a desired product and co-oxidizing by-product partially oxidized carbon oxide into carbon dioxide, especially co-oxidizing carbon monoxide to carbon dioxide. In the case of propane oxidation, the inventors have found that the dual function catalyst compositions of this invention efficiently convert propane to acrylic acid, while simultaneously converting by-product CO to $CO_2$, thereby reducing the build up of CO in a recycle stream. After testing a number of auxiliary metals in a standard base catalyst composition, the inventors have found that the addition of a relatively small amount of platinum (Pt), within a specific range, to the base catalyst composition produces effective and efficient dual function catalyst compositions. While the addition of Pt at all levels tested, even relatively low or minor levels, resulted in a minor decrease in catalyst activity and selectivity, these decreases were more than offset by the catalysts ability to oxidize. The reduction in CO production via co-oxidation eliminates the need to remove CO from the recycle stream. In addition, the use of Pt levels that are higher than the levels described herein are disadvantageous in terms of both catalyst performance and catalyst cost.

The dual function catalyst compositions of this invention are capable of oxidizing propane to acrylic acid and carbon monoxide to carbon dioxide under both propane limiting reaction conditions and oxygen limiting reaction conditions.

The dual function catalyst compositions have a selectivity to acrylic acid (AA) of at least 55%, have a conversion of propane of at least 20% and produce carbon oxides in a ratio of $CO/CO_2 \leq 1.00$ under propane limiting conditions. In other embodiments, the catalyst compositions have a selectivity to acrylic acid (AA) of at least 55%, have a conversion of propane of at least 20% and produce carbon oxides in a ratio of $CO/CO_2 \leq 0.75$ under propane limiting conditions. In other embodiments, the catalyst compositions have a selectivity to acrylic acid (AA) of at least 55%, have a conversion of propane of at least 20% and produce carbon oxides in a ratio of $CO/CO_2 \leq 0.50$ under propane limiting conditions. In other embodiments, the catalyst compositions have a selectivity to acrylic acid (AA) of at least 55%, have a conversion of propane of at least 20% and produce carbon oxides in a ratio of $CO/CO_2 \leq 0.25$ under propane limiting conditions. In other embodiments, the catalyst compositions have a selectivity to acrylic acid (AA) of at least 55%, have a conversion of propane of at least 20% and produce carbon oxides in a ratio of $CO/CO_2 \leq 0.15$ under propane limiting conditions. In other embodiments, the catalyst compositions have a selectivity to acrylic acid (AA) of at least 55%, have a conversion of propane of at least 20% and produce carbon oxides in a ratio of $CO/CO_2 \leq 0.10$ under propane limiting conditions. In other embodiments, the catalyst compositions have a selectivity to acrylic acid (AA) of at least 60%, have a conversion of propane of at least 25% and produce carbon oxides in a ratio of $CO/CO_2 \leq 0.50$ under propane limiting conditions. In other embodiments, the catalyst compositions have a selectivity to acrylic acid (AA) of at least 65%, have a conversion of propane of at least 25% and produce carbon oxides in a ratio of $CO/CO_2 \leq 0.25$ under propane limiting conditions. In other embodiments, the catalyst compositions have a selectivity to acrylic acid (AA) of at least 70%, have a conversion of propane of at least 25% and produce carbon oxides in a ratio of $CO/CO_2 \leq 0.20$ under propane limiting conditions. In other embodiments, the catalyst compositions have a selectivity to acrylic acid (AA) of at least 70%, have a conversion of propane of at least 25% and produce carbon oxides in a ratio of $CO/CO_2 \leq 0.15$ under propane limiting conditions. In other embodiments, the catalyst compositions have a selectivity to acrylic acid (AA) of at least 70%, have a conversion of propane of at least 25% and produce carbon oxides in a ratio of $CO/CO_2 \leq 0.10$ under propane limiting conditions.

Suitable Reagents and Components

Alkanes

Suitable alkanes for oxidation with the catalyst compositions of this invention include, without limitation, $C_3$ to $C_5$ alkanes. Exemplary non-limiting examples include, without limitation, propane, n-butane, isobutane, n-pentane, iso-pentane, or mixtures thereof.

Metals Components

It should be understood that the starting materials provided herein are exemplary and not exhaustive. Suitable starting materials (metal sources) for Mo, V and Nb oxides are for instance those described in U.S. Pat. No. 5,380,933 (col. 3, line 27 to 57) and/or U.S. Pat. No. 6,710,207 (col. 8, lines 12 to 30), and include organic and inorganic salts and acids (normally oxyacids) of the desired metal elements. The salts are selected in a manner that after calcining only metal elements and oxygen remain in the calcined catalyst precursor, because all other constituents are volatile or rendered volatile by decomposition or oxidation. For this reason, the use of ammonium salts of the metal element (or the corresponding oxyacid), organic salts such as oxalates, alkoxides or acetylacetonates, organic metal complexes, metalorganic compounds or volatile inorganic salts such as nitrates are also suitable. Moreover, the selected salts and acids are generally soluble or at least dispersible in the selected solvent such as water. Suitable starting salts and acids include for instance ammonium para- or heptamolybdate, molybdenum oxalate, molybdophosphoric acid, telluric acid, bismuth nitrate, ammonium metavanadate, vanadium oxalate, vanadyl sulfate ($VOSO_4$), ammonium niobium oxalate, ammonium para- or heptatungstate, tungsten oxalate, tungstophosphoric acid, and ammonium tantalum oxalate. For example, the catalyst may be prepared by forming a solution of the V source (e.g., an aqueous ammonium metavanadate solution) and a solution of the Te source (e.g., an aqueous solution of telluric acid) and adding them to a solution of the Mo source (e.g., an aqueous solution of ammonium heptamolybdate), optionally after heating the Mo solution, followed by the addition of the solution of a Nb source (e.g., an aqueous solution of ammonium niobium oxalate). Similarly, a suitable starting material for the optional Z element may be selected by a skilled person from those used in the art. Manganese (Mn) may for instance be added as manganese acetate and ruthenium (Ru) as polyacid, for instance Mo-containing (optionally also P-containing) polyacids such as $H_3PMo_{11}RuO_{40}$.

Generally, the amounts of starting materials are adjusted as precisely as possible to produce a catalyst having nominally the amount of metals set forth in a particular catalyst formula as the precise starting material amounts appear to have a great impact on the activity of the target catalyst. The concentration (by mol) of each metal existing in the starting composition should not differ more than ±5% from the calculated composition for a given catalyst composition. In certain embodiments, the concentrations of starting metals should not differ by more than ±2%. In other embodiments, the concentrations of starting metals should not differ by more than ±1%. In other embodiments, the concentrations of starting metals should not differ by more than 0.5%. In other embodiments, the concentrations of starting metals should not differ by more than 0.1% by mol.

Non-Ionic (Neutral) Templating Agent

In certain preparation methods of the present invention, the non-ionic (neutral) templating agent may be present in the solution or slurry provided as a template for pore formation in the final catalyst compositions. The shape and size of the templating agent determine the shape and size of the pores present in the catalyst compositions of this invention.

Suitable templating agents including, without limitation, Lewis bases, i.e., compounds that possess a free electron pair present, for instance, in compounds having an ether bond, where a free electron pair is present at the respective oxygen atom. The templating agents used in the preparation of catalyst compositions of this invention are broadly classified into neutral templating agents (i.e., agents that do not dissociate into ions in water) and charged templating agents (i.e., agents carrying a charge before or after dissociation in water, such as salts, for instance CTAB). In certain embodiments of this invention, neutral templating agents are used in catalyst preparation.

Suitable neutral templating agents include, without limitation, compounds that do not carry a positive or negative charge or that do not dissociate in the solvent to species that carry a positive or negative charge. Exemplary non-limiting examples of neutral templating agents include oxygen-containing copolymers, such as poly(alkylene oxide) polymers, for instance poly(ethylene oxide), triblock copolymers of the poly(alkylene oxide) type, such as those of the ethylenoxide/propylenoxide/ethylenoxide type, or diblock copolymers of the poly(alkylene oxide) type, such as those of the ethylenoxide/butylenoxide-type. These polymers are available under the tradename Pluronic.

As discussed above, the size and shape of the templating agent determines the structure of the resulting mesoporous material and ultimately, influences the pore size distribution of the final catalyst compositions. Accordingly, the pore size may be tuned by adjusting the size of the templating agent. In the case of polyalkylene oxide templating agents pore size is influenced by the molecular weight. In certain embodiments, the polyalkylene oxide templating agents have a number average molecular weight of 1,100 to 15,000.

Other usable non-ionic templating agents are surfactant-based agents, such as primary amines, e.g., those of the formula $C_nH_{2n+1}NH_2$, wherein n is an integer of 12 to 18 and $C_nH_{2n+1}$ represents a branched or, preferably, a linear alkyl group, or alcohols, such as primary alcohols, e.g. those of the formula $C_nH_{2n+1}OH$, wherein n is an integer of 12 to 18 and $C_nH_{2n+1}$ represents a branched or, preferably, a linear alkyl group.

The relative proportions of the templating agent and the metal precursors in the mixture provided is not specifically limited, generally ranges from 0.001 to 0.03 expressed as molar amount of templating agent/molar amount of metal precursors.

Solvents

In the catalyst composition preparation steps of this invention, the above-described metal precursors generally involve solutions or slurries of one or more metal starting material. The type of the solvent used in this regard is not particularly limited, as long as it can dissolve the metal precursors at least to some degree. If a pressure-resistant vessel is used, it is sufficient if the solvent used can dissolve the metal precursors at least to some degree under conditions in the pressure-resistant vessel. For example, a solvent may be used which does not dissolve the metal precursors under standard conditions (room temperature and 1 atm pressure), but which does dissolve the metal precursors at least to some degree in the pressure-resistant vessel at elevated pressures and/or temperatures.

Suitable solvents include, without limitation, water and/or one or more polar solvents, such as protic solvents, e.g., alcohols (e.g., methanol, ethanol, isopropanol), or aprotic solvents, such as ketones (e.g., acetone) or ethers (e.g., dimethylether, diethylether, di-t-.butylether). In certain embodiments, the solvent comprises water or an aqueous solution. When water or an aqueous solution is used, the solution or slurry may be denoted as an "aqueous" solution or slurry.

Besides the metal precursors, the templating agent and the solvent, the solutions or slurries may contain various additives. Such additives may be used to tailor the pore size of the resulting catalyst compositions. For example, templating agents may be used to increase pore size. Other additives may include agents that complex metals or that increase metal starting material solubility. Suitable complexing or solubility enhancing additives may include citric acid, oxalic acid or EDTA (ethylene diamine tetra acetic acid). Other additives including reducing agents, such as hydrazine or hydroxylamine may be used to control the oxidation state of the metal in the synthesis. Oxalic acid is a useful additive to adjust the oxidation state of tellurium, when the synthesis is performed in a pressure resistant vessel or during thermal treatment. Solids, which are not dissolved under the synthesis conditions in the pressure resistant vessel, may be added as diluents. Examples are particles of oxides like silica, SiC or carbon, such as activated carbon or nanostructured carbon, such as carbon nanotubes or nanofibres.

Experiments of the Invention

Catalyst 1 Preparation

Catalyst 1 was prepared having the nominal composition of $Mo_1V_{0.3}Nb_{0.12}Sb_{0.09}Te_{0.09}O_x$, where x is a number need to balance the valencies of the catalyst composition.

Solution A was prepared as follows: 40.0 g of ammonium para molybdate were dissolved in 300 mL water with heating. 7.95 g of ammonium vanadate were added next and dissolved upon stirring for 30 minutes. 4.68 g of telluric acid dihydrate were added next and dissolved. 2.97 g of antimony (III) oxide were added next. The solution was heated at 90° C. for 1 hour and then allowed to cool to 35° C.

Solution B was prepared as follows: 20.6 g of oxalic acid dihydrate were dissolved in 150 mL of warm water with heating. 4.7 g of niobic acid were added and the solution was heated to a temperature between 95° C. and 100° C. for one hour. Solution B was then cooled to room temperature.

Solution B was added to Solution A. The resulting solution was spray dried to give a solid catalyst precursor. The catalyst precursor was heated in air at 120° C. for 1 hr, then decomposed at 300° C. for 5 hrs. The catalyst precursor was then calcined in argon at 600° C. for 2 hrs. The resulting powder was ground, pressed, and sieved to 18/35 mesh to yield the active catalyst, Catalyst 1.

Catalysts 2-4 Preparation

Catalysts 2-4 include Ag, Ga and Pd, respectively, and were prepared to have a nominal compositions of $Mo_1V_{0.3}NB_{0.12}Sb_{0.09}Te_{0.09}M_eO_x$, where x is a number need to balance the valencies of the catalyst composition, with the amount of M set forth below:

| Cat. | M  | y    | Starting Material         | Amount (g) | Water    |
|------|----|------|---------------------------|------------|----------|
| 2    | Ag | 0.05 | silver nitrate            | 1.92       | none     |
| 3    | Ga | 0.05 | gallium oxide             | 1.06       | none     |
| 4    | Pd | 0.05 | tetraamine palladium (II) nitrate | 3.38 | 10 wt. % |

Solution A was prepared as follows: 40.0 g of ammonium para molybdate were dissolved in 300 mL water with heating. 7.95 g of ammonium vanadate were added and dissolved upon stirring for 30 minutes. 4.68 g of telluric acid dihydrate were added and dissolved. 2.97 g of antimony (III) oxide were added. Finally, the designated grams of M were added in each case as described in the table above. The Solution was heated at 90° C. for 1 hour then allowed to cool to 35° C.

Solution B was prepared as follows: 20.6 g Oxalic acid dihydrate were dissolved in 150 mL of warm water with heating. 4.7 g of niobic acid were added. The solution was covered and heated to a temperature between 95° C. and 100° C. for one hour. Solution B was cooled to room temperature.

Solution B was added to Solution A. The resulting solution was spray dried to give a solid catalyst precursor. The catalyst precursor was heated in air at 120° C. for 1 hr, then decomposed at 300° C. for 5 hrs. The decomposed catalyst precursor was then calcined in argon at 600° C. for 2 hrs. The resulting powder was ground, pressed, and sieved to 18/35 mesh to yield the active catalysts, Catalysts 2-4.

Catalyst 5 Preparation

Catalyst 5 was prepared having the nominal composition of $Mo_1V_{0.3}Nb_{0.12}Sb_{0.09}Te_{0.09}Pt_{0.05}O_x$, where x is a number need to balance the valencies of the catalyst composition.

Solution A was prepared as follows: 40.0 g of ammonium para molybdate were dissolved in 270 mL water with heating. 7.95 g of ammonium vanadate were added next and dissolved upon stirring for 30 minutes. 4.68 g of telluric acid dihydrate were added next and dissolved. 2.97 g of antimony (III) oxide were added. 4.39 g of tetraamine platinum (II) nitrate were dissolved in 45 mL of water and then added to this solution. The solution was heated at 90° C. for 1 hour and then cooled to 35° C.

Solution B was prepared as follows: 20.6 g of oxalic acid dihydrate were dissolved in 150 mL of warm water with heating. 4.7 g of niobic acid were added and the solution was heated to a temperature between 95° C. and 100° C. for one hour. Solution B was cooled to room temperature.

Solution B was added to Solution A. The resulting solution was spray dried to give a solid catalyst precursor. The catalyst precursor was heated in air at 120° C. for 1 hr, and then decomposed at 300° C. for 5 hrs. The catalyst precursor was then calcined in argon at 600° C. for 2 hrs. The resulting powder was ground, pressed, and sieved to 18/35 mesh to yield the active catalyst, Catalyst 5.

Catalysts 6-8 Preparation

Catalysts 6-8 include differing amount of Pt and were prepared to have a nominal compositions of $Mo_1V_{0.3}Nb_{0.12}Sb_{0.09}Te_{0.09}Pt_yO_x$, $Mo_1V_{0.3}Nb_{0.12}Sb_{0.09}Te_{0.09}O_x$, where x is a number need to balance the valencies of the catalyst composition and y is the amount of Pt set forth below:

| Cat. | y | Starting Material | Amount (g) | Water (mL) |
|---|---|---|---|---|
| 6 | 0.013 | tetraamine platinum (II) nitrate | 1.10 | 45 |
| 7 | 0.006 | tetraamine platinum (II) nitrate | 0.55 | 45 |
| 8 | 0.003 | tetraamine platinum (II) nitrate | 0.27 | 45 |

Solution A was prepared as follows: 40.0 g of ammonium para molybdate were dissolved in 270 mL water with heating. 7.95 g of ammonium vanadate were added and dissolved upon stirring for 30 minutes. 4.68 g of telluric acid dihydrate were added and dissolved. 2.97 g of antimony (III) oxide were added. Finally, y grams of tetraamine platinum (II) nitrate (as described in the table above) were dissolved in 45 mL water were added to this solution. The solution was heated at 90° C. for 1 hour then allowed to cool to 35° C.

Solution B was prepared as follows: 20.6 g of oxalic acid dihydrate were dissolved in 150 mL of warm water with heating. 4.7 g of niobic acid were added. The solution was covered and heated to a temperature between 95° C. and 100° C. for one hour. Solution B was cooled to room temperature.

Solution B was added to Solution A. The resulting solution was spray dried to give a solid catalyst precursor. The catalyst precursor was heated in air at 120° C. for 1 hr, then decomposed at 300° C. for 5 hrs, then calcined in argon at 600° C. for 2 hrs. The resulting powder was ground, pressed, and sieved to 18/35 mesh, to yield the active catalysts, Catalysts 6-8.

Catalyst Testing

Figure 2:
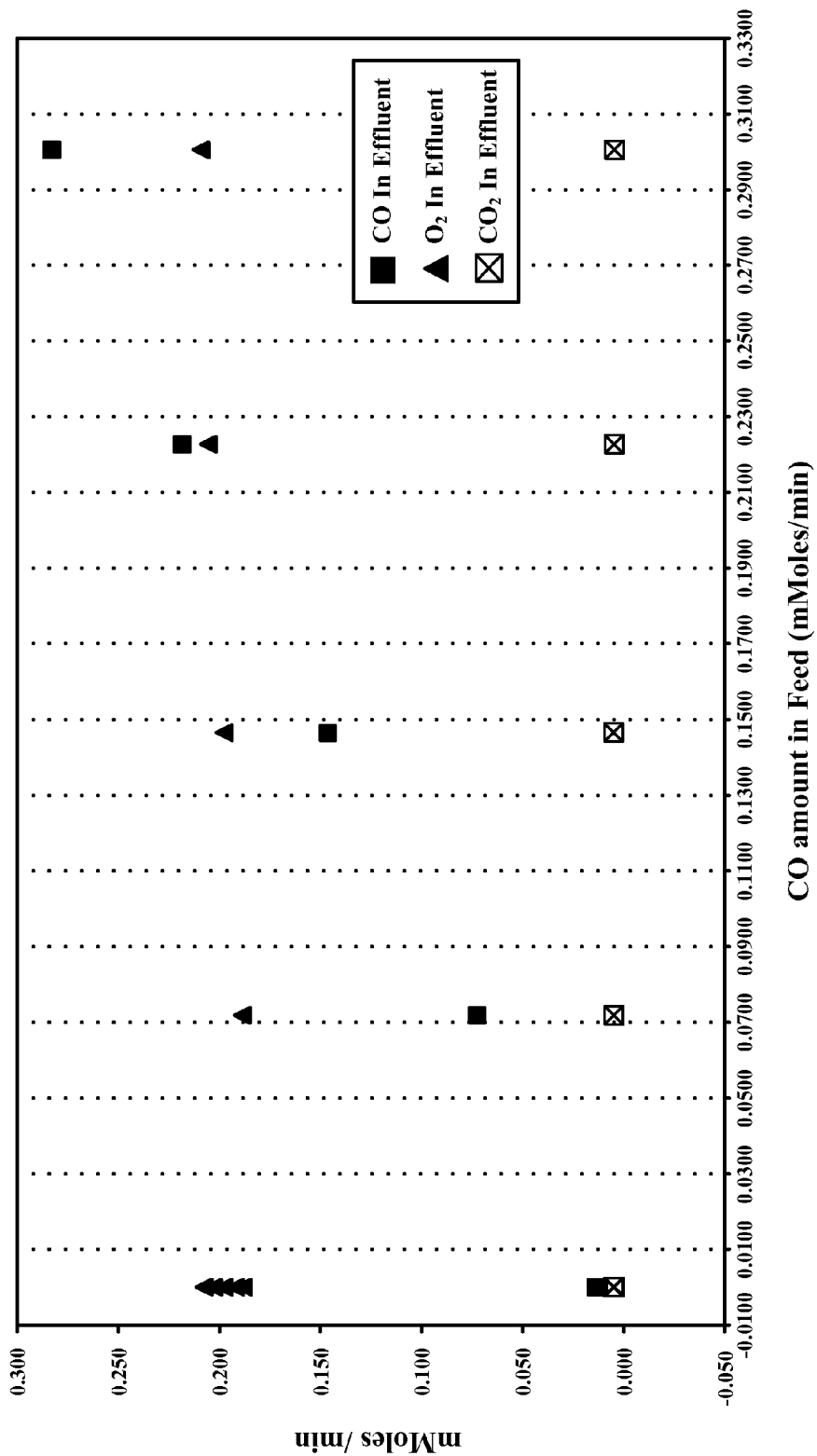
FIG. 2 depicts CO oxidation performance of Catalyst 1.

We tested the performance of the base catalyst $MoV_{0.3}Nb_{0.12}Sb_{0.09}Te_{0.09}$, Catalyst 1, for CO oxidation to $CO_2$ under propane oxidation conditions with an $O_2$ to propane ratio of 0.5, oxygen limiting conditions. The CO oxidation test was performed as indicated in Table 1 and the results are shown in FIG. 1 & FIG. 2.

TABLE I

Reactor Feed Composition for CO Experiments at $O_2$ to Propane Ratio of 0.5

| Feed SCCM | | | | | | % in Feed | | | | |
|---|---|---|---|---|---|---|---|---|---|---|
| Propane SCCM | $O_2$ SCCM | $N_2$ SCCM | CO SCCM | Steam SCCM | Total | Propane % | $O_2$ % | $N_2$ % | CO % | Steam % |
| 20.0 | 10 | 90 | 0 | 65 | 185 | 10.8 | 5.4 | 48.7 | 0.0 | 35.0 |
| 20.0 | 10 | 90 | 2 | 65 | 187 | 10.7 | 5.4 | 48.2 | 1.1 | 34.7 |
| 20.0 | 10 | 90 | 4 | 65 | 189 | 10.6 | 5.3 | 47.7 | 2.1 | 34.3 |
| 20.0 | 10 | 90 | 6 | 65 | 191 | 10.5 | 5.2 | 47.2 | 3.1 | 33.9 |
| 20.0 | 10 | 90 | 8 | 65 | 193 | 10.4 | 5.2 | 46.7 | 4.2 | 33.6 |

The data indicated that Catalyst 1 did not co-oxidize CO to $CO_2$ under oxygen limiting propane oxidation conditions as shown graphically in FIG. 1. The data also showed that as the amount of CO was increased in the feed, the amount of CO increased in the effluent. Additionally, the Net CO($CO_{out}$−$CO_{in}$) amount showed little decrease as the amount of CO was increased in the feed. Moreover, there was no significant increase in the amount of $CO_2$ in the effluent or a significant decrease in the amount of $O_2$ in the effluent, when the amount of CO was increased as shown graphically in FIG. 2. These facts taken together indicated that the base catalyst, Catalyst 1, did not convert CO to $CO_2$ under oxygen limiting propane oxidation conditions. The tests were all performed at a propane ratio of 0.5, oxygen limiting conditions, with flow rates of all components kept constant except for the CO flow rate, which varied from 0 Standard Cubic Centimeters per Minute (SCCM) to 8 SCCM. The total flow rate increased from 185 SCCM to 193 SCCM due to the increase in the CO flow rate.

Catalyst Modification

We chose to modify Catalyst 1 by adding metals that we believed would produce catalyst compositions capable of the simultaneous partial alkane oxidation and co-oxidation of CO. The metals we tested were Ag, Ga, Pd and Pt. These metals were chosen for their oxidation characteristics. The compositions and the physical properties of modified catalyst, Catalyst 2-5, which included Ag, Ga, Pd and Pt, respectively, are given Table II.

TABLE II

Physical properties of Modified $MoV_{0.3}Nb_{0.12}Sb_{0.09}Te_{0.09}X_m$

| Catalyst ID | 1 | 2 | 3 | 4 | 5 |
|---|---|---|---|---|---|
| $X_m$ | none | $Ag_{0.05}$ | $Ga_{0.05}$ | $Pd_{0.05}$ | $Pt_{0.05}$ |
| Ball milled | yes | yes | yes | yes | yes |
| SA (m²/g) | 10.9 | 8.8 | 10 | 11.8 | 11.5 |
| PV (CC/g) | 0.074 | 0.065 | 0.074 | 0.09 | 0.08 |
| APS | 270 | 294 | 270 | 305 | 279 |
| X-light size A | 377 | 648 | 591 | 578 | 455 |
| XRF | | | | | |

TABLE II-continued

Physical properties of Modified $MoV_{0.3}Nb_{0.12}Sb_{0.09}Te_{0.09}X_m$

| Catalyst ID | 1 | 2 | 3 | 4 | 5 |
|---|---|---|---|---|---|
| Te | 5.33 | 5.21 | 5.35 | 5.05 | 5.26 |
| Sb | 6.26 | 5.72 | 6.04 | 5.87 | 6.02 |
| Mo | 48.17 | 47.32 | 47.25 | 47.52 | 47.28 |
| Nb | 5.24 | 5.12 | 5.14 | 5.4 | 5.29 |
| V | 7.16 | 6.93 | 7.08 | 7.34 | 7.15 |
| Other metal | | 2.17 (Ag) | 1.452 (Ga) | N/A | 0.06 (Pt) |

Figure 3:
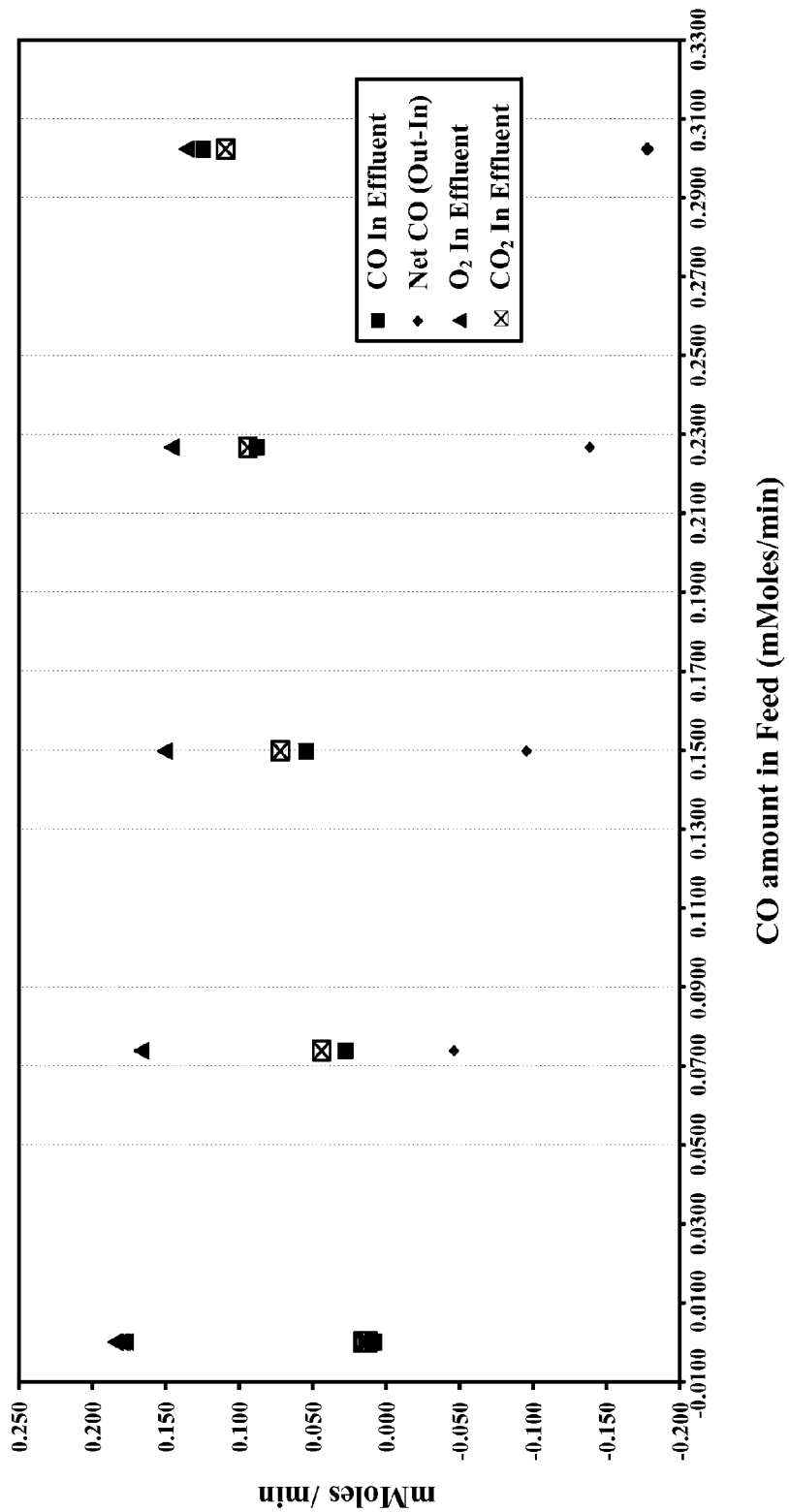
FIG. 3 depicts CO oxidation performance of Catalyst 5.

Catalysts 2-5 were tested for propane oxidation under propane limiting reaction conditions, oxygen to propane ratio of 3 and under oxygen limiting reaction conditions, oxygen to propane ratio of 0.5. A summary of performance data for Catalysts 2-5 compared to the performance of Catalyst 1 are tabulated in Table III.

tion conditions of Table I are presented graphically in FIG. 3. It is evident from FIG. 3 that as the amount of CO was increased in the feed, the amount of $CO_2$ increased in the effluent. Moreover, the "Net CO" (Out−in) decreased as the amount of CO was increased in the feed. The amount of $O_2$ in the effluent also decreased as the amount of CO was increased in the feed. This data strongly supports the determination that $O_2$ is reacting with CO to form $CO_2$ under propane oxidation conditions set forth in Table I.

Comparative Testing of Catalyst 1 and Catalyst 5

Figure 4:
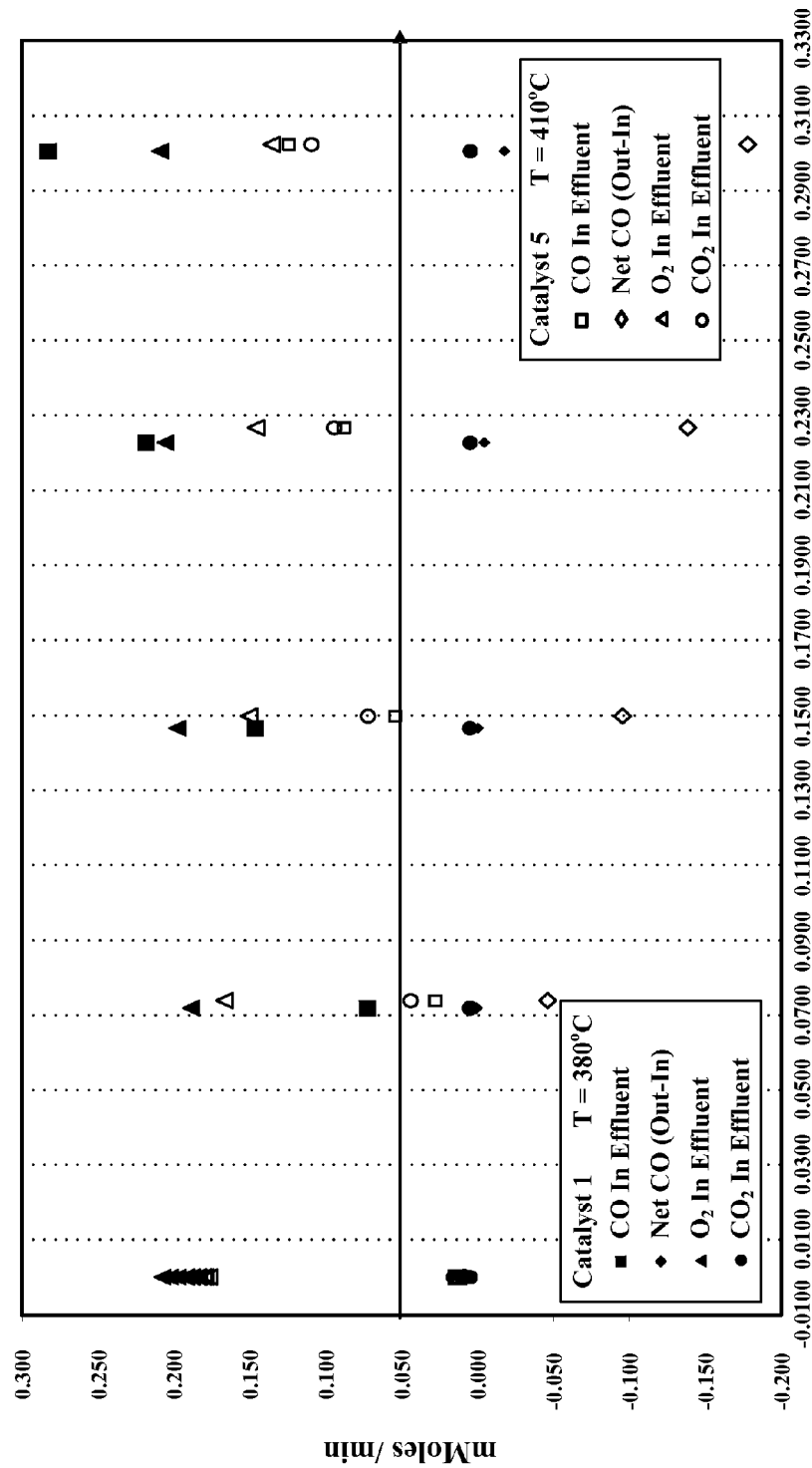
FIG. 4 depicts CO oxidation performance of Catalyst 1 vs. Catalyst 5.

The performance of Catalyst 5 for CO co-oxidation was compared to that of the base catalyst, Catalyst 1. It is clear from FIG. 4 that Catalyst 5 showed a superior ability to co-oxidize CO under propane oxidation conditions than Catalyst 1. Thus, Catalyst 5 will work to oxidize CO to $CO_2$ therefore allowing CO to be removed as $CO_2$ in a recycle process, hence avoiding expensive CO removal alternatives.

TABLE III

Propane Oxidation Performance of Catalysts 2-5 Compared to Catalyst 1

| Cat | Loading (g) | T °C. | SV-g[†] | GHSV[‡] | Conv. % | $O_2$ Conv. Wt. % | % $CO_x$ | % Sel $C_3$= | % Sel AA | Kg AA/ $m^3$Cat-hr | $CO/CO_2$ | CO | $CO_2$ |
|---|---|---|---|---|---|---|---|---|---|---|---|---|---|
| Propane-Limiting Conditions: $C_3:O_2:N_2:H_2O$ = 1:3:27:14, 32 psig ||||||||||||||
| 1 | 0.78 | 410 | 0.59 | 16493 | 41.2 | 30.1 | 14.3 | 8.6 | 65.9 | 339 | 2.2 | 9.8 | 4.5 |
| 2 | 0.77 | 410 | 0.59 | 16487 | 25.3 | 24.1 | 15.7 | 12.4 | 63.9 | 232 | 3.3 | 12 | 3.6 |
| 3 | 0.76 | 410 | 0.6 | 16486.8 | 36.1 | 31.6 | 12.4 | 8.3 | 68.5 | 360 | 3.5 | 9.6 | 2.8 |
| 4 | 0.76 | 410 | 0.61 | 16563 | 28.6 | 19.9 | 10.6 | 13.0 | 67.7 | 282 | 2.4 | 7.5 | 3.1 |
| 5 | 0.77 | 410 | 0.60 | 16563.2 | 26.5 | 22.1 | 14.3 | 13.4 | 61.0 | 238 | 0.1 | 1.7 | 12.6 |
| Oxygen-Limiting Conditions: $C_3:O_2:N_2:H_2O$ = 1:0.5:4.5:3.5, 32 psig ||||||||||||||
| 1 | 0.78 | 400 | 3.59 | 20760 | 16.9 | 69.9 | 5.5 | 20.6 | 59.6 | 904 | 2.3 | 3.8 | 1.6 |
| 2 | 0.77 | 410 | 3.51 | 20875 | 10.4 | 42.5 | 7.4 | 32.7 | 50.5 | 440 | 3.2 | 5.8 | 1.8 |
| 3 | 0.76 | 410 | 3.55 | 20874.7 | 17.6 | 73.1 | 6 | 20.3 | 61.1 | 921 | 3.1 | 4.6 | 1.5 |
| 4 | 0.76 | 410 | 3.69 | 20824 | 14.0 | 54.0 | 4.8 | 27.1 | 57.5 | 706 | 2.4 | 3.3 | 1.4 |
| 5 | 0.77 | 410 | 3.65 | 20823.7 | 12.6 | 53.1 | 5.7 | 28.7 | 54.8 | 607 | 0.7 | 2.3 | 3.3 |

[†]propane/g cat-hr;
[‡]L gas/L cat-hr.

All propane oxidation experiments were performed using a constant catalyst volume of 0.5 CC. In all cases, the addition of the auxiliary metal slightly deceased catalyst activity, when compared to Catalyst 1 under both propane limiting and oxygen limiting reaction conditions as evidenced from the propane conversion data given in Table III. The addition of Ag and Pd, Catalyst 2 and Catalyst 4, lowered the catalyst activity the most, while Ga, Catalyst 3, affected the activity the least. Upon examination of the CO to $CO_2$ ratios of the effluent stream for each of the modified catalysts as evidence in Table III, the Pt modified catalyst, Catalyst 5 stands out. Surprisingly, in the case of Catalyst 5, the CO to $CO_2$ ratio ranged from 0.1 to 0.7, while the CO to $CO_2$ ratio ranged from 2.2 to 3.5 for all of the other catalysts. Thus, Catalyst 5, the platinum modified catalyst, was determined to be a good candidate for simultaneously oxidation of CO to $CO_2$ under propane oxidation conditions regardless of whether the conditions were propane or oxygen limited. The results were unexpected as all four auxiliary metals have oxidation characteristics that made them good candidates of the co-oxidation of CO under propane oxidation conditions, but only platinum showed this capability when added in low levels to the base catalyst, Catalyst 1.

Figure 5:
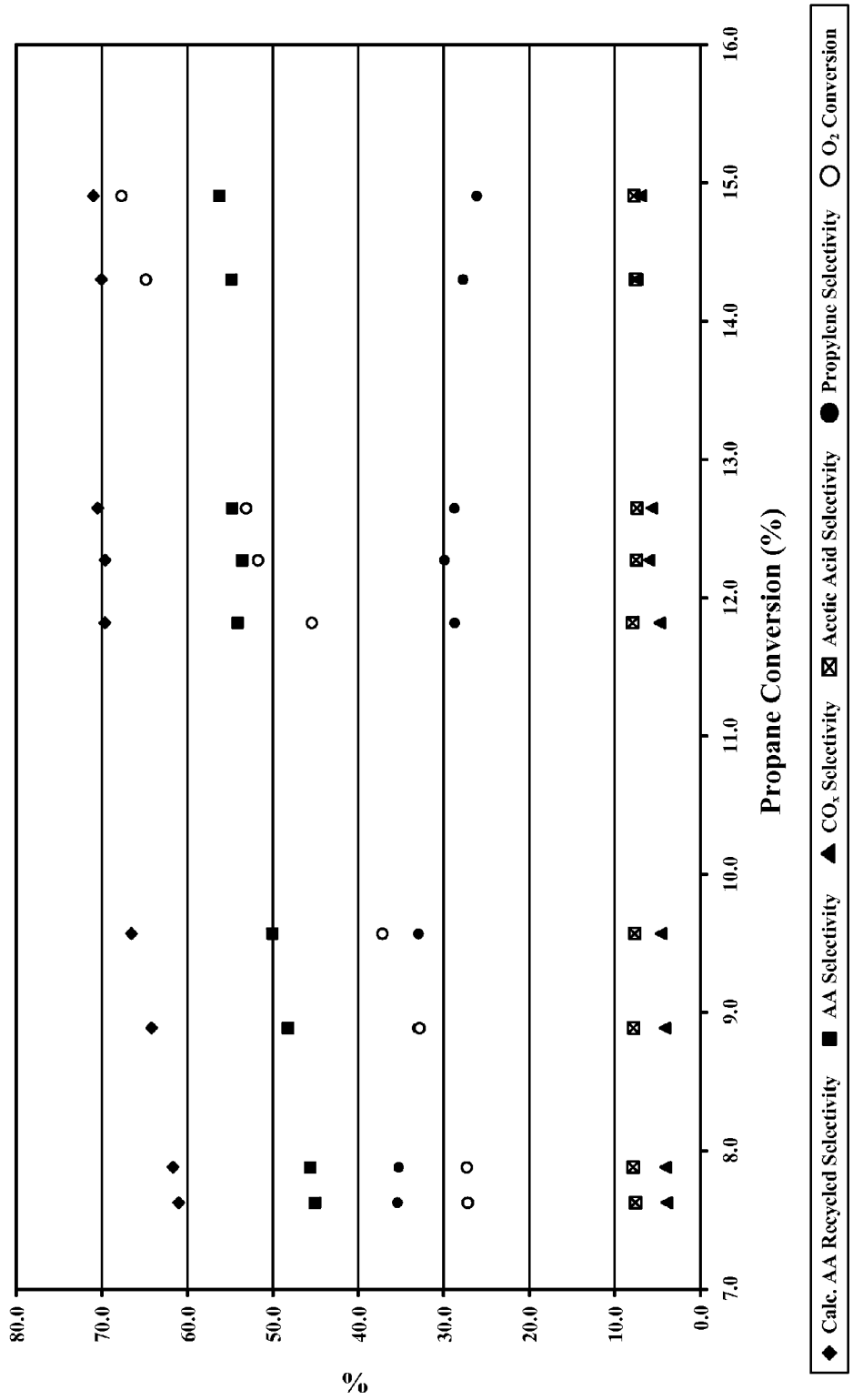
FIG. 5 depicts performance of Catalyst 5 at $O_2$ to propane ratio of 0.5.
Figure 6:
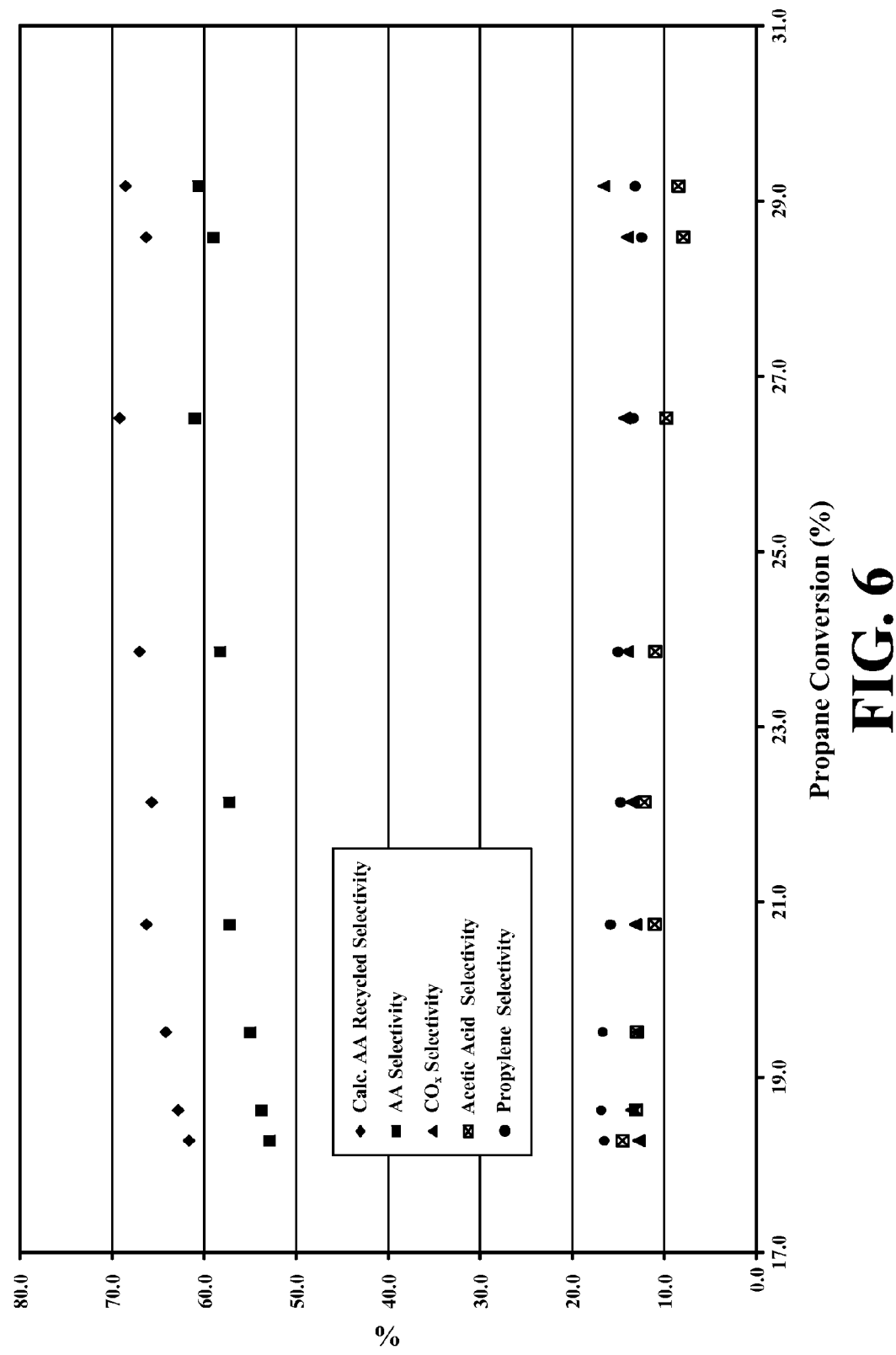
FIG. 6 depicts performance of Catalyst 5 at $O_2$ to propane ratio of 3.

Next, the Pt modified catalyst, Catalyst 5, was tested at 410° C. for CO oxidation under propane oxidation conditions given in Table I, the condition used to test the base catalyst, Catalyst 1, which had been tested at 380° C. The performance data of Catalyst 5 for CO co-oxidation under propane oxida- Complete catalyst performance of Catalyst 5 and Catalyst 1 were conducted under both oxygen limiting conditions and propane limiting conditions. The results of the complete catalyst performance testing of Catalyst 5 under oxygen limiting conditions and propane limiting conditions are shown graphically FIG. 5 and FIG. 6, respectively. Similarly, the results of the complete catalyst performance testing of Catalyst 1 under oxygen limiting conditions and propane limiting conditions are shown graphically FIG. 7 and FIG. 8, respectively. Catalyst 5 showed only a small decrease in catalyst activity and selectivity compared to Catalyst 1 under both oxygen limiting conditions and propane limiting conditions. In these tests, the amount of catalyst tested was 0.5 mL, which corresponded to 0.77 grams of Catalyst 5 and 0.78 grams of Catalyst 1. The catalyst bed was 3 mL diluted by quartz to make up the catalyst bed volume. Catalyst 5 and Catalyst 1 were tested at a temperature between 370° C. and 420° C. at a pressure of 32 psig. The oxygen limiting conditions were a $C_3/O_2/H_2O/N_2$ ratio of 1/0.5/3.5/4.5 (10.5%/5.3%/38.6%/47.4%) at flow rates of $C_3/O_2+N_2/H_2O$ of 20 SCCM/100 SCCM/0.052 mL liquid. The propane limiting conditions were a $C_3/O_2/H_2O/N_2$ ratio of 1/3/14/27 (2.2%/6.7%/31.1%/60%) at flow rates of $C_3/O_2+N_2/H_2O$ of 3.3 SCCM/100 SCCM/0.035 mL liquid. It should be noted that the Calculated AA Selectivity (Calc. AA Recycle Selective as shown in the Figures) is a theoretical value calculated from the observed single pass catalyst performance. The reaction effluents were analyzed by gas chromatography, so that the single pass AA production value is a measured value as are all of the other single pass starting material and products.

Varying Platinum Concentration

Catalyst 5 contained approximately 4.5 wt. % platinum. We varied the amount of platinum in the catalyst to determine how platinum concentration affected CO to $CO_2$ conversion under propane oxidation conditions. We prepared several platinum containing catalysts in which the platinum weight percentage (wt. %) was varied in a range between 4.5 wt. % and 0.3 wt. %. Catalysts were prepared as described above having: 1.2 wt. % platinum, Catalyst 6; 0.6 wt. % platinum, Catalyst 7; and 0.3 wt. % platinum, Catalyst 8. The physical properties of Catalyst 5-8 are tabulated in Table IV and compared to the physical properties of Catalyst 1.

TABLE IV

Physical properties of Modified $MoV_{0.3}Nb_{0.12}Sb_{0.09}Te_{0.09}Pt_m$

| Catalyst | 5 | 6 | 7 | 8 | 1 |
|---|---|---|---|---|---|
| m | $Pt_{0.05}$ | $Pt_{0.013}$ | $Pt_{0.006}$ | $Pt_{0.003}$ | none |
| Ball milled | yes | yes | yes | yes | yes |
| SA (m²/g) | 11.5 | 13.9 | 11.3 | 11.5 | 10.9 |
| PV (CC/g) | 0.08 | 0.076 | 0.068 | 0.071 | 0.074 |
| APS | 279 | 219 | 239 | 248 | 270 |
| X-light size A | 455 | 497 | 880 | 516 | 377 |

TABLE IV-continued

Physical properties of Modified $MoV_{0.3}Nb_{0.12}Sb_{0.09}Te_{0.09}Pt_m$

| Catalyst | 5 | 6 | 7 | 8 | 1 |
|---|---|---|---|---|---|
| | | | XRF | | |
| Te | 5.26 | 5.43 | 5.56 | 5.39 | 5.33 |
| Sb | 6.02 | 6.05 | 6.14 | 6.19 | 6.26 |
| Mo | 47.28 | 48.09 | 47.98 | 47.91 | 48.17 |
| Nb | 5.29 | 5.29 | 5.20 | 5.26 | 5.24 |
| V | 7.15 | 7.20 | 7.14 | 7.11 | 7.16 |
| Theoretical Pt % wt | 4.5 | 1.2 | 0.6 | 0.3 | 0 |

The XRF data showed that the Te, Sb, Mo, Nb and V concentration were similar as are the PV values. The surface areas of ball milled Catalysts 5, 7 and 8 are approximately 11 m²/g, which is similar to that of Catalyst 1, while Catalyst 6 had a surface area of 13.9. The X-light size A does show marked differences of the platinum modified catalyst, Catalyst 5-8, compared to Catalyst 1.

The performance of the platinum modified catalysts, Catalyst 5-8, for propane oxidation was tested under two propane oxidation conditions: propane limiting conditions, an oxygen to propane ratio of 3:1 and oxygen limiting conditions, an oxygen to propane ratio of 0.5:1. The results of these tests are summarized in Table V and Table VI.

TABLE V

Summary of the Performance of Catalysts 5-8 Compared to Catalyst 1

| Catalyst | 5 | 6 | 7 | 8 | 1 | 5 | 6 | 7 | 8 | 1 |
|---|---|---|---|---|---|---|---|---|---|---|
| Theoretical Pt % wt | 4.5 | 1.2 | 0.6 | 0.3 | 0 | 4.5 | 1.2 | 0.6 | 0.3 | 0 |
| Catalyst Wt g | 0.77 | 0.72 | 0.76 | 0.78 | 0.78 | 0.77 | 0.72 | 0.76 | 0.78 | 0.78 |
| Volume = 0.5 CC | | | | | | | | | | |
| Feed Composition | Propane-Limiting Conditions: $C_3/O_2/H_2O/N_2 = 1/3/14/27$ | | | | | Oxygen-Limiting Conditions: $C_3/O_2/H_2O/N_2 = 1/0.5/3.5/4.5$ | | | | |
| Catalyst Bed TEMP (° C.) | 400 | 400 | 400 | 400 | 400 | 400 | 400 | 400 | 400 | 400 |
| Pressure Psig | 32 | 32 | 32 | 32 | 32 | 32 | 32 | 32 | 32 | 32 |
| Wt. % Propane Conversion | 23.9 | 32.2 | 34.0 | 34.3 | 34.1 | 11.8 | 14.6 | 13.5 | 15.7 | 16.8 |
| Wt. % Oxygen Conversion | 18.6 | 27.4 | 28.6 | 29.9 | 28.6 | 45.4 | 57.5 | 62.2 | 66.1 | 73.2 |
| SELECTIVITY | | | | | | | | | | |
| COx | 14.0 | 10.5 | 9.6 | 10.8 | 11.0 | 4.8 | 4.4 | 4.7 | 4.6 | 6.7 |
| Propylene | 15.0 | 9.7 | 8.8 | 9.2 | 9.4 | 28.7 | 25.4 | 25.2 | 23.9 | 22.2 |
| Acetic Acid | 11.0 | 8.6 | 9.2 | 9.1 | 10.3 | 7.9 | 6.5 | 6.6 | 7.0 | 8.8 |
| Acrylic Acid | 58.3 | 69.4 | 70.6 | 69.3 | 67.3 | 54.1 | 59.9 | 58.5 | 61.1 | 57.8 |
| ACRYLIC ACID YIELD | 13.9 | 22.3 | 24.0 | 23.8 | 22.9 | 6.4 | 8.7 | 7.9 | 9.6 | 9.7 |
| Recycled Selectivity | 67.0 | 76.1 | 76.8 | 75.6 | 73.6 | 69.6 | 75.1 | 73.3 | 75.6 | 70.6 |

TABLE VI

Summary of the Performance of Catalysts 5-8 Compared to Catalyst 1

| Cat. | Loading | T ° C. | SV-g† | GHSV‡ | % C | Wt. % $O_2$ Conv. | % $CO_x$ | % Sel $C_3$ | % Sel AA | Kg AA/ m³Cat-hr | CO/$CO_2$ | CO | $CO_2$ |
|---|---|---|---|---|---|---|---|---|---|---|---|---|---|
| | | | | Propane Limiting Conditions: $C_3:O_2:N_2:H_2O = 1:3:27:14$, 32 psig | | | | | | | | | |
| 5 | 0.77 | 400 | 0.60 | 16563.2 | 23.9 | 18.6 | 14.0 | 15.0 | 58.3 | 199 | 0.1 | 1.6 | 12.4 |
| 5 | 0.77 | 410 | 0.60 | 16563.2 | 26.5 | 22.1 | 14.3 | 13.4 | 61.0 | 238 | 0.1 | 1.7 | 12.6 |
| 6 | 0.72 | 400 | 0.64 | 16526.6 | 32.2 | 27.4 | 10.5 | 9.7 | 69.4 | 329 | 0.24 | 2.0 | 8.4 |
| 6 | 0.72 | 410 | 0.64 | 16433.3 | 34.6 | 29.7 | 11.4 | 9.7 | 70.2 | 348 | 0.301 | 2.6 | 8.7 |
| 7 | 0.76 | 400 | 0.61 | 16502.1 | 34.0 | 28.6 | 9.6 | 8.8 | 70.6 | 339 | 0.146 | 1.2 | 8.3 |
| 7 | 0.76 | 410 | 0.61 | 16502.1 | 37.0 | 32.3 | 10.6 | 7.6 | 71.1 | 386 | 0.155 | 1.4 | 9.2 |
| 8 | 0.78 | 400 | 0.59 | 16486.8 | 34.3 | 29.9 | 10.8 | 9.2 | 69.3 | 339 | 0.404 | 3.1 | 7.7 |
| 8 | 0.78 | 410 | 0.59 | 16486.8 | 37.5 | 33.7 | 11.5 | 8.5 | 71.1 | 388 | 0.471 | 3.7 | 7.8 |
| 1 | 0.78 | 410 | 0.59 | 16493 | 41.2 | 30.1 | 14.3 | 8.6 | 65.9 | 339 | 2.2 | 9.8 | 4.5 |
| | | | | Oxygen Limiting Conditions: $C_3:O_2:N_2:H_2O = 1:0.5:4.5:3.5$, 32 psig | | | | | | | | | |
| 5 | 0.77 | 400 | 3.65 | 20830.7 | 11.8 | 45.4 | 4.8 | 28.7 | 54.1 | 550 | 0.8 | 2.0 | 2.7 |
| 5 | 0.77 | 410 | 3.65 | 20823.7 | 12.6 | 53.1 | 5.7 | 28.7 | 54.8 | 607 | 0.7 | 2.3 | 3.3 |

TABLE VI-continued

Summary of the Performance of Catalysts 5-8 Compared to Catalyst 1

| Cat. | Loading | T °C. | SV-g† | GHSV‡ | % C | Wt. % $O_2$ Conv. | % $CO_x$ | % Sel $C_3$ | % Sel AA | Kg AA/ m³Cat-hr | $CO/CO_2$ | CO | $CO_2$ |
|---|---|---|---|---|---|---|---|---|---|---|---|---|---|
| 6 | 0.72 | 400 | 3.90 | 20760.4 | 14.6 | 57.5 | 4.4 | 25.4 | 59.9 | 749 | 1.062 | 2.2 | 2.1 |
| 6 | 0.72 | 410 | 3.90 | 20751.6 | 15.4 | 65.9 | 5.1 | 25.1 | 60.4 | 815 | 0.907 | 2.4 | 2.7 |
| 7 | 0.76 | 400 | 3.70 | 20827.4 | 13.5 | 62.2 | 4.7 | 25.2 | 58.5 | 710 | 0.912 | 2.2 | 2.4 |
| 7 | 0.76 | 410 | 3.71 | 20873.4 | 14.6 | 70.1 | 4.9 | 24.4 | 60.2 | 809 | 0.826 | 2.2 | 2.7 |
| 8 | 0.78 | 400 | 3.57 | 20928.7 | 15.7 | 66.1 | 4.6 | 23.9 | 61.1 | 821 | 0.936 | 2.2 | 2.4 |
| 8 | 0.78 | 410 | 3.57 | 20928.7 | 17.9 | 78.5 | 5.7 | 21.1 | 62.8 | 988 | 1.2 | 3.1 | 2.6 |
| 1 | 0.78 | 400 | 3.59 | 20760 | 16.9 | 69.9 | 5.5 | 20.6 | 59.6 | 904 | 2.3 | 3.8 | 1.6 |

†propane/g cat-hr;
‡L gas/L cat-hr.

It is clear from the data set forth in Table V that large amounts of platinum (4.5 wt. %) has a slight adverse effect on the performance of the catalyst. However, platinum amounts smaller than 1 wt. % did not adversely affect catalyst performance relative to Catalyst 1. Additionally, catalysts having Pt levels greater than 4.5 wt. % are less advantageous both from a catalyst performance perspective and a catalyst cost perspective.

Under propane limiting condition test results given in Table VI, the $CO/CO_2$ ratio in the effluent for Catalyst 8, which contains the least amount of platinum tested (0.3 wt. %), was about 0.47, while $CO/CO_2$ ratio for the base catalyst, Catalyst 1, under the same conditions was 2.2. It can be concluded from the data presented in Table VI that propane oxidation catalysts with small amounts of platinum are effective in co-oxidizing CO to $CO_2$ under propane limiting conditions, with little or no adverse affects on catalyst activity or selectivity. Thus, the dual function activity of platinum modified catalyst may be achieved at relatively low platinum concentrations, which affords a considerable cost benefit to the dual function catalyst of this invention.

Similarly, under oxygen limiting condition test results given in Table VI, the $CO/CO_2$ ratio in the effluent for Catalyst 8 is 1.2, while the $CO/CO_2$ ratio for the base catalyst, Catalyst 1, under the same conditions is 2.3. It can be concluded from the data presented in Table VI that catalysts having relatively small amounts of platinum are effective in co-oxidizing CO to $CO_2$ even under oxygen limiting conditions.

Figure 9:
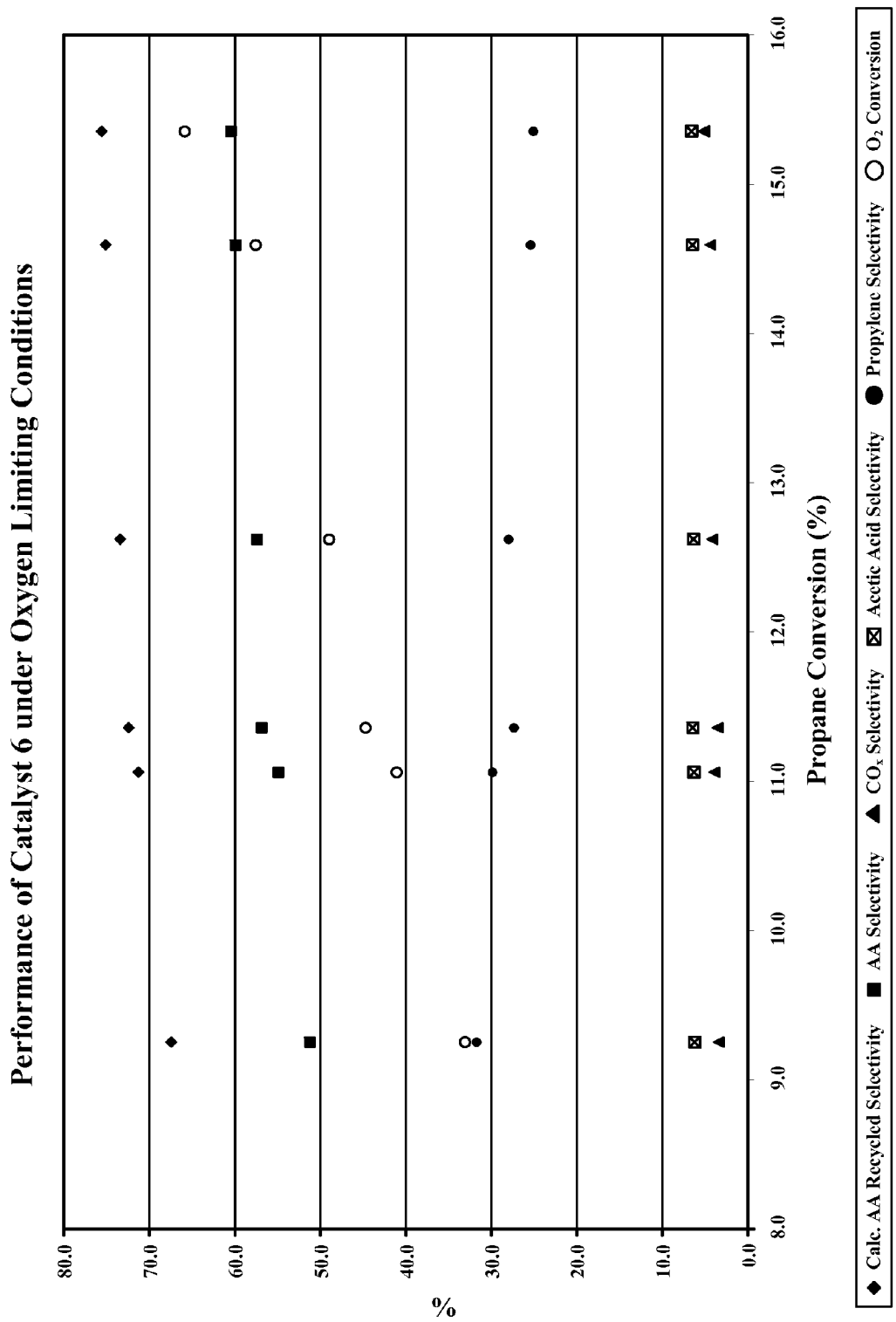
FIG. 9 depicts performance of Catalyst 6 at $O_2$ to propane ratio of 0.5.
Figure 10:
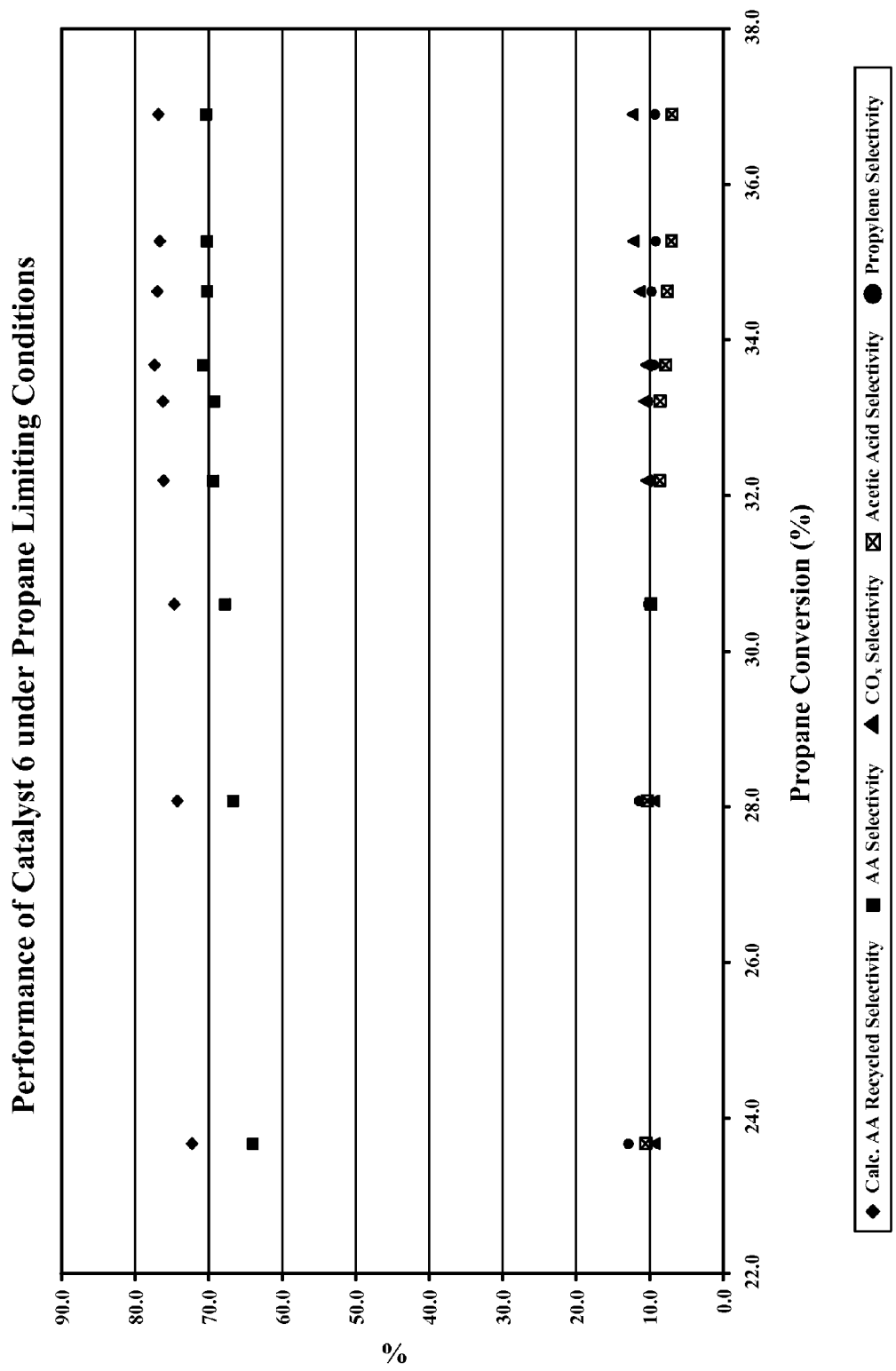
FIG. 10 depicts performance of Catalyst 6 at propane to $O_2$ ratio of 3.
Figure 11:
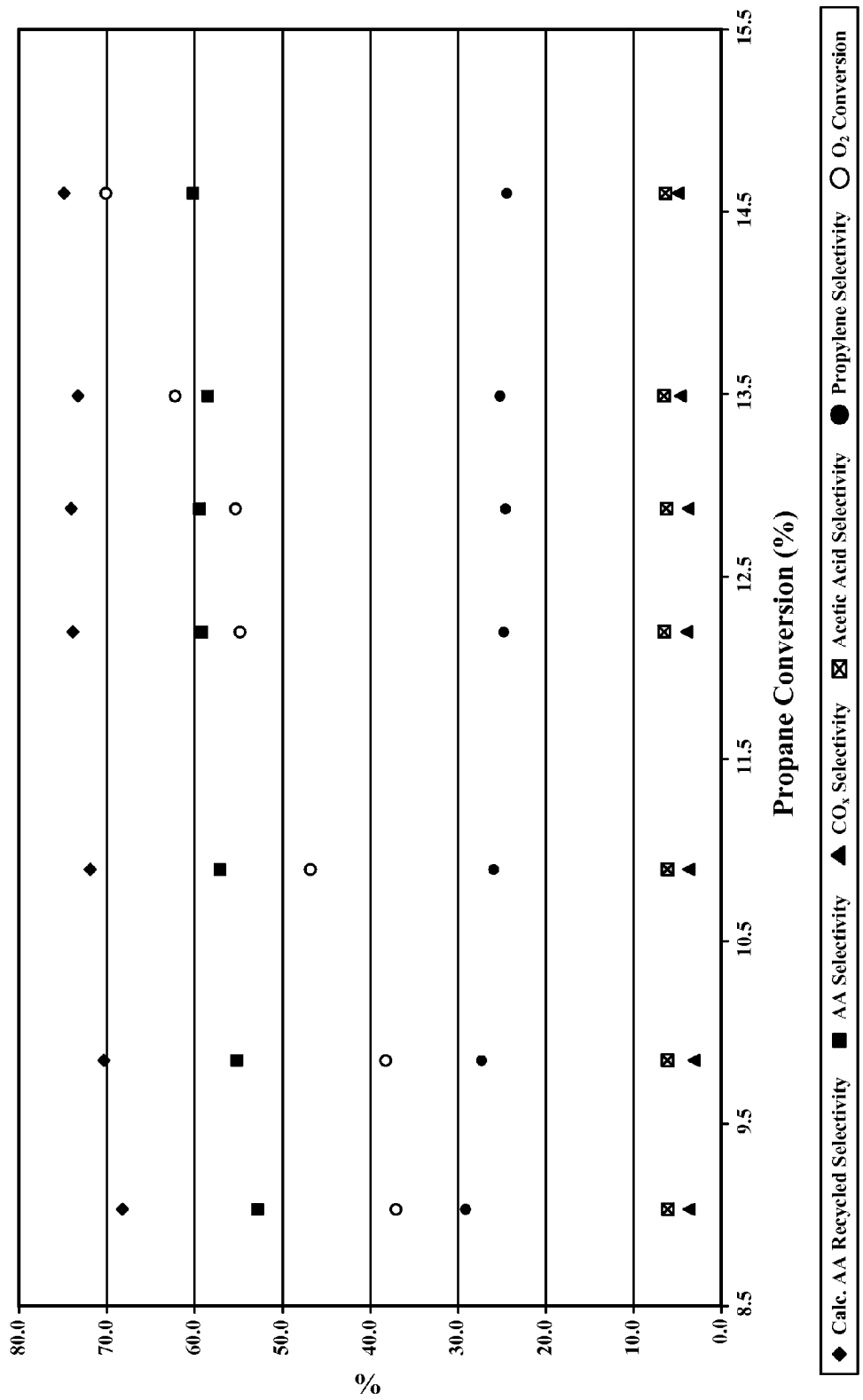
FIG. 11 depicts performance of Catalyst 7 at $O_2$ to propane ratio of 0.5.
Figure 12:
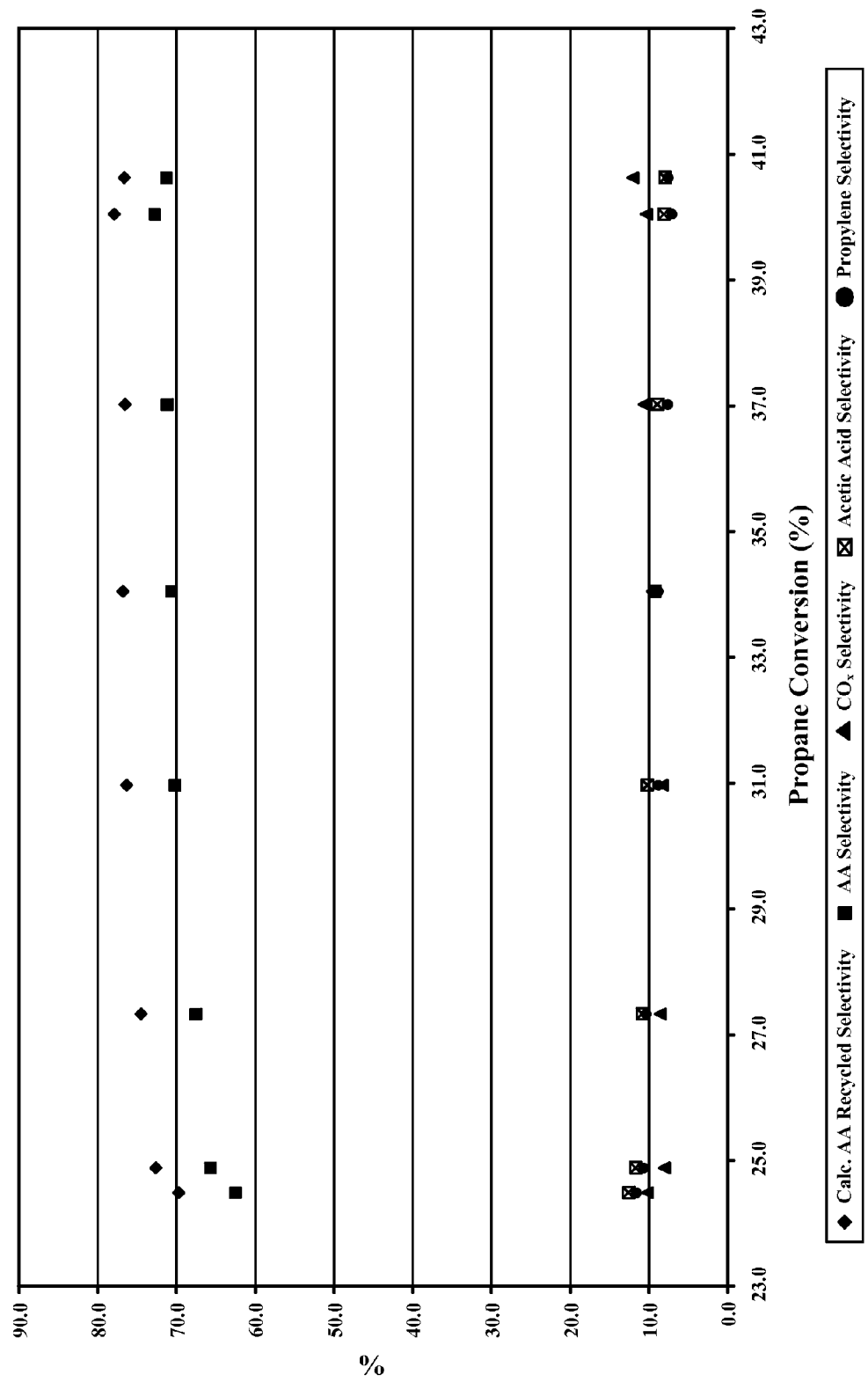
FIG. 12 depicts performance of Catalyst 7 at propane to $O_2$ ratio of 3.
Figure 13:
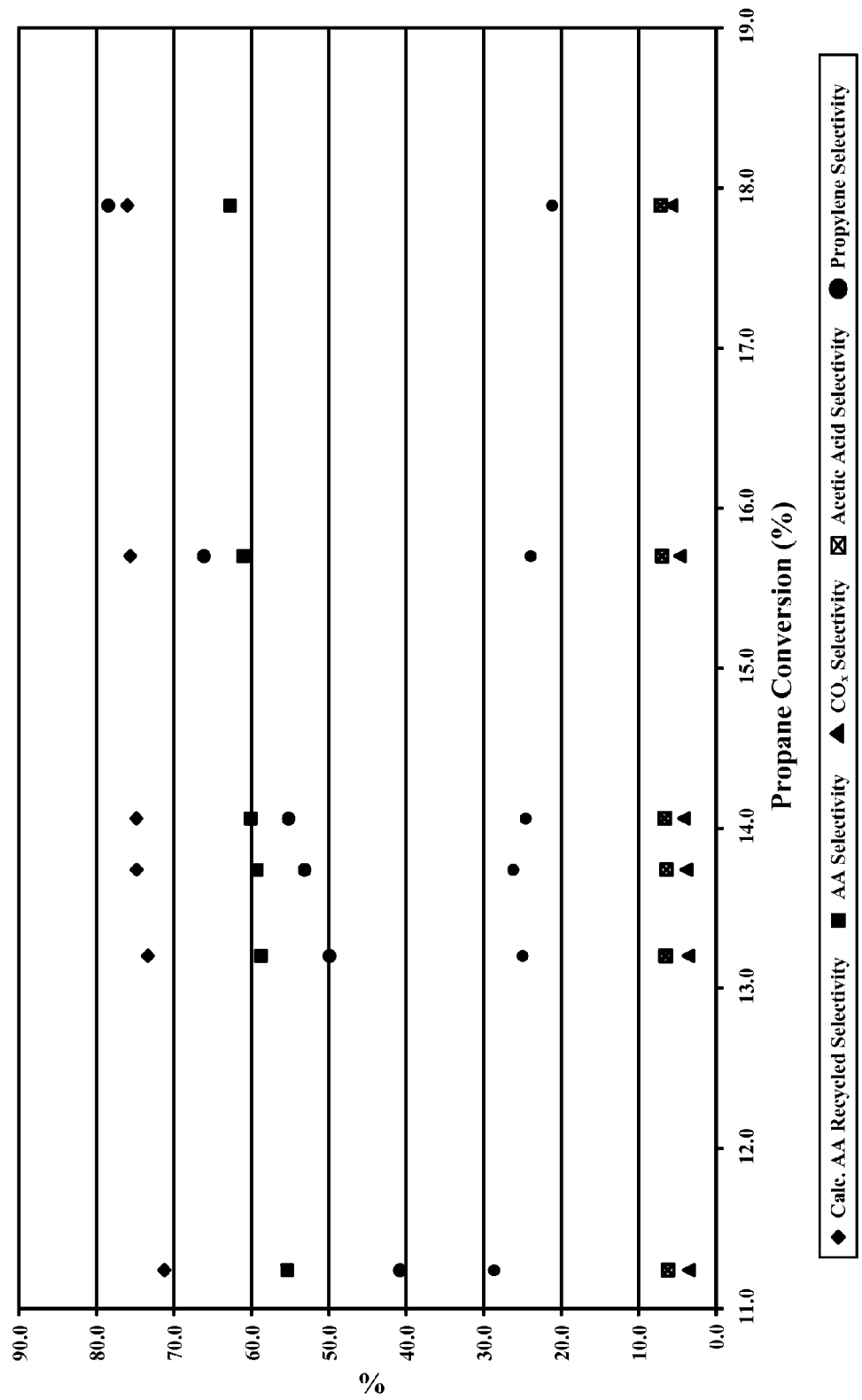
FIG. 13 depicts performance of Catalyst 8 at $O_2$ to propane ratio of 0.5.
Figure 14:
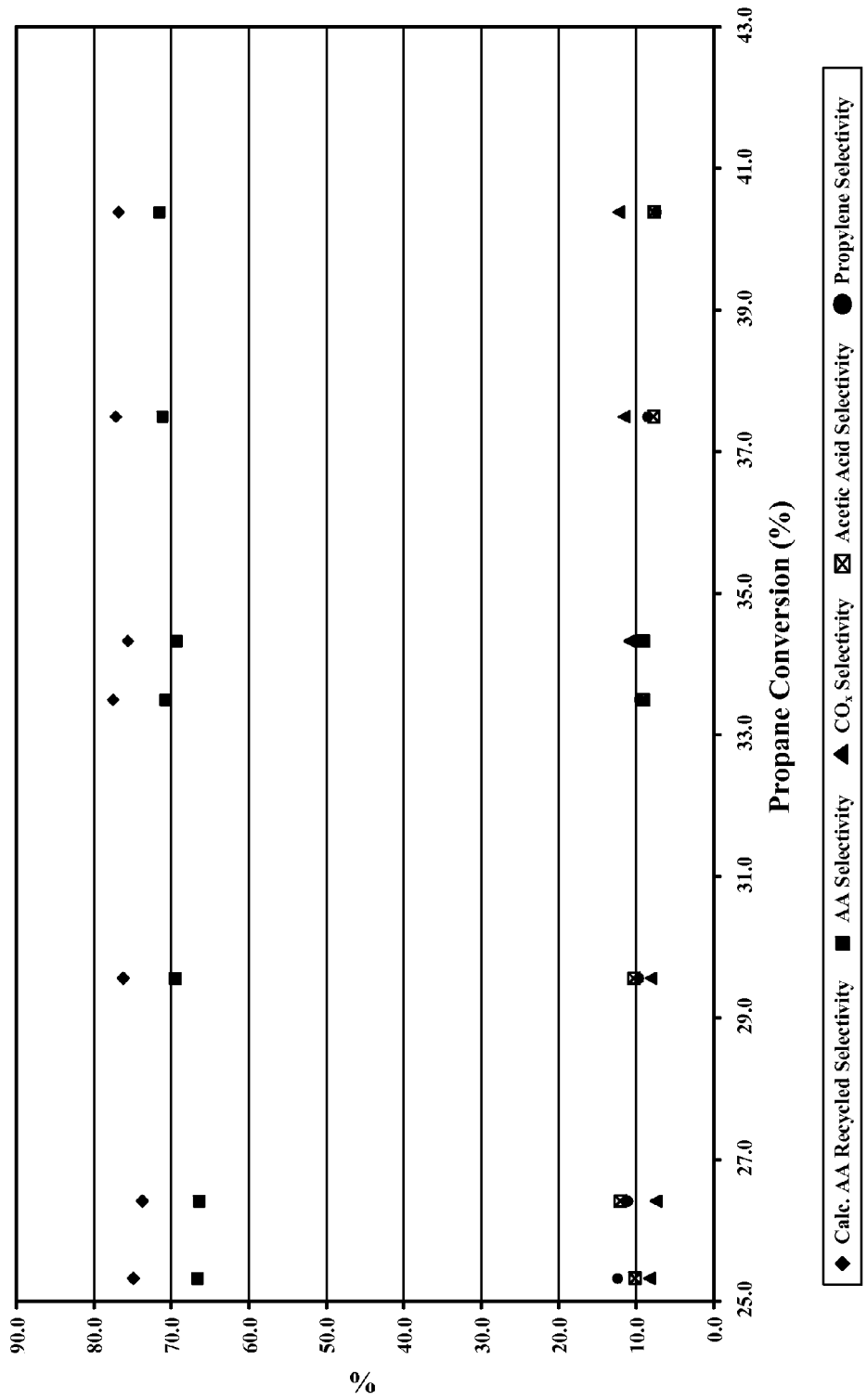
FIG. 14 depicts performance of Catalyst 8 at propane to $O_2$ ratio of 3.

The full performance of Catalyst 6 for propane oxidation under oxygen-limiting conditions and propane limiting conditions are also depicted graphically in FIG. 9 and FIG. 10. The full performance of Catalyst 7 for propane oxidation under oxygen-limiting conditions and propane limiting conditions are also depicted graphically in FIG. 11 and FIG. 12. And the full performance of Catalyst 8 for propane oxidation under oxygen-limiting conditions and propane limiting conditions are also depicted graphically in FIG. 13, and FIG. 14. In these tests, the amount of catalyst tested was 0.5 mL, which corresponded to 0.72 grams of Catalyst 6, 0.76 grams of Catalyst 7, and 0.78 grams of Catalyst 8. The catalyst bed was 3 mL diluted by quartz to make up the catalyst bed volume. Catalyst 6-8 were tested at a temperature between 370° C. and 420° C. at a pressure of 32 psig. The oxygen limiting conditions were a $C_3/O_2/H_2O/N_2$ ratio of 1/0.5/3.5/4.5 (10.5%/5.3%/38.6%/47.4%) at flow rates of $C_3/O_2+N_2/H_2O$ of 20 SCCM/100 SCCM/0.052 mL liquid. The propane limiting conditions were a $C_3/O_2/H_2O/N_2$ ratio of 1/3/14/27 (2.2%/6.7%/31.1%/60%) at flow rates of $C_3/O_2+N_2/H_2O$ of 3.3 SCCM/100 SCCM/0.035 mL liquid.

Figure 7:
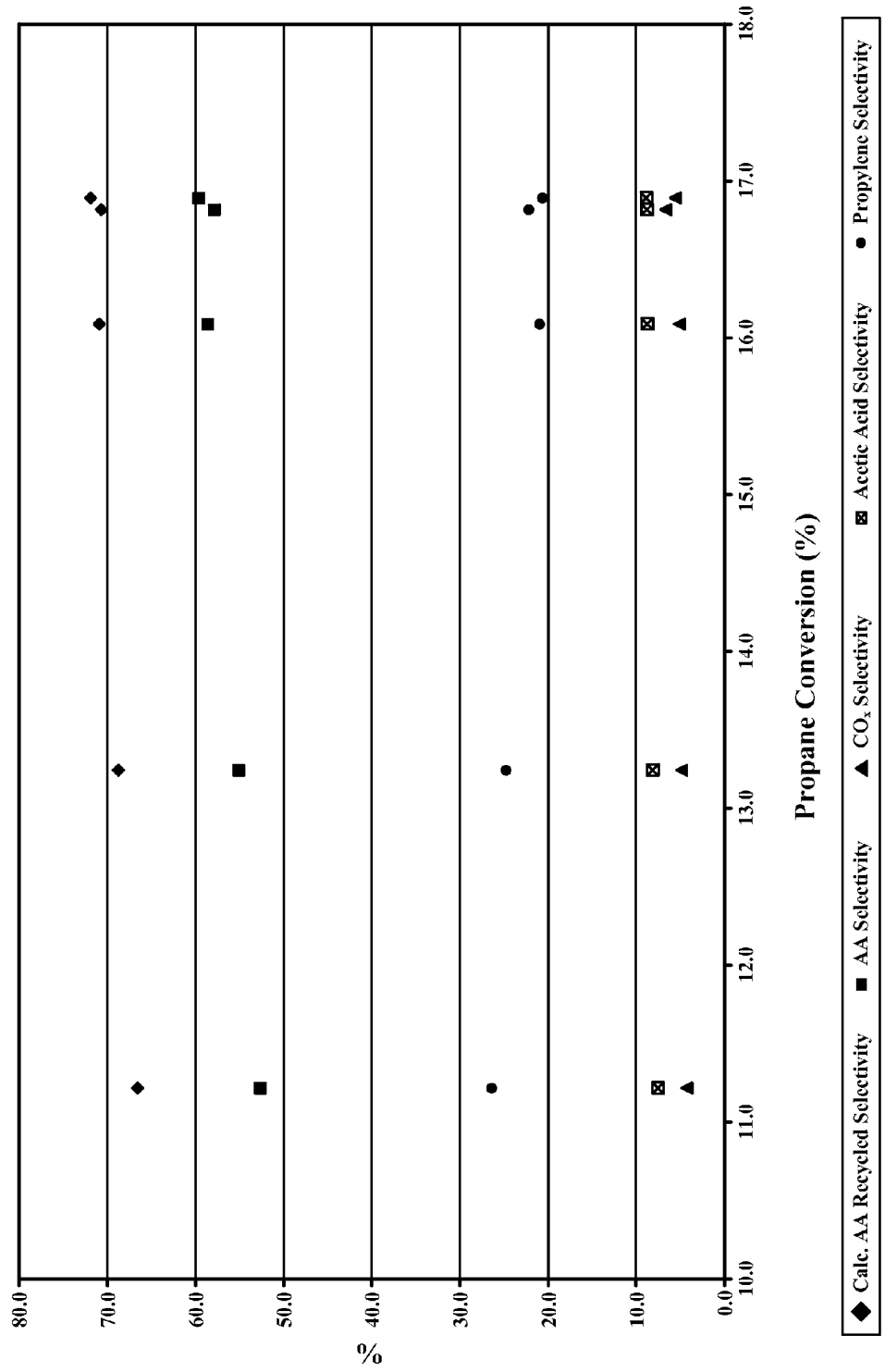
FIG. 7 depicts performance of Catalyst 1 at $O_2$ to propane ratio of 0.5.
Figure 8:
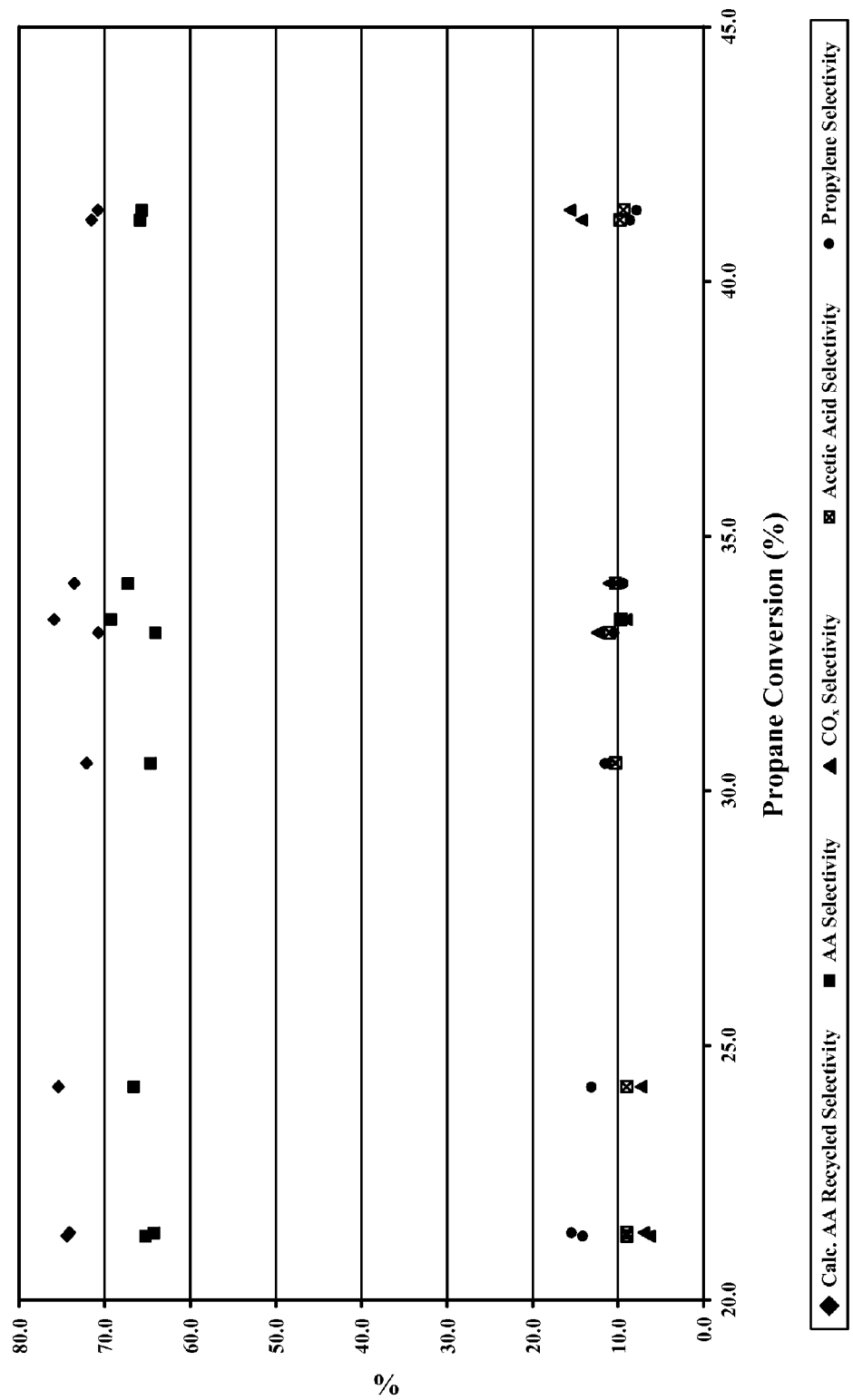
FIG. 8 depicts performance of Catalyst 1 at propane to $O_2$ ratio of 3.

It is clear from these figures that performance of catalyst modified with small amounts of platinum (1 wt. % or less) is similar to that of Catalyst 1 as depicted graphically in FIG. 7 and FIG. 8. Thus, in certain embodiments of this invention, the catalysts of this invention include a platinum wt. % or less than or equal to about 1 wt. %. In other embodiments, the platinum wt. % is less than or equal to about 0.8 wt. %. In other embodiments, the platinum wt. % is less than or equal to about 0.6 wt. %. In other embodiments, the platinum wt. % is less than or equal to about 0.5 wt. %. In other embodiments, the platinum wt. % is less than or equal to about 0.4 wt. %. In other embodiments, the platinum wt. % is less than or equal to about 0.3 wt. %. It is clearly evident from the data present herein that propane oxidation catalyst having relative small amounts of platinum are capable of co-oxidizing CO to $CO_2$ in situ during propane oxidation. The use of relatively small amount of platinum to modify the base catalyst has to advantages: 1) minimization of the cost of platinum needed and 2) simplification of the process by reducing CO production and build up.

Figure 15:
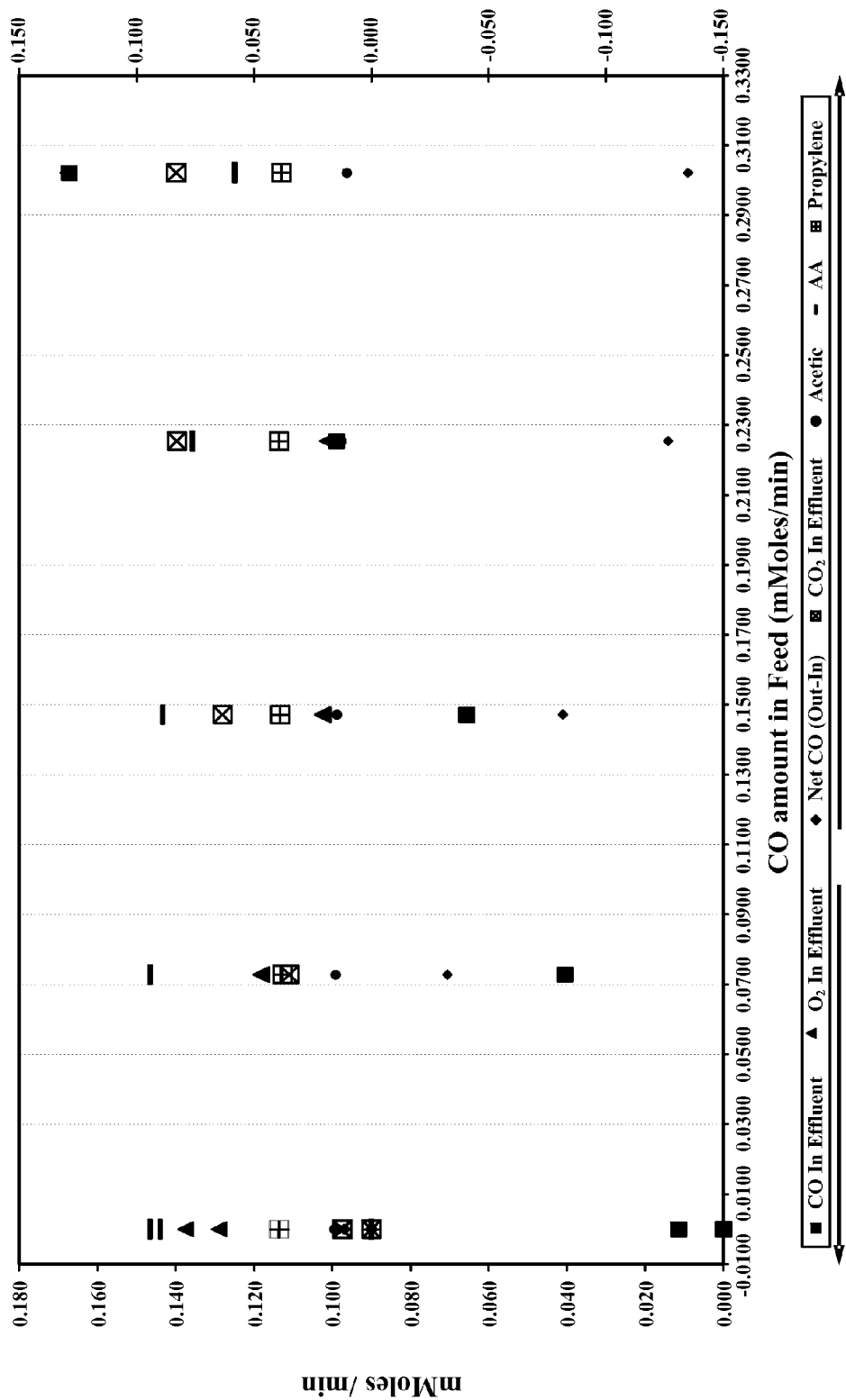
FIG. 15 depicts CO oxidation performance of Catalyst 6.
Figure 16:
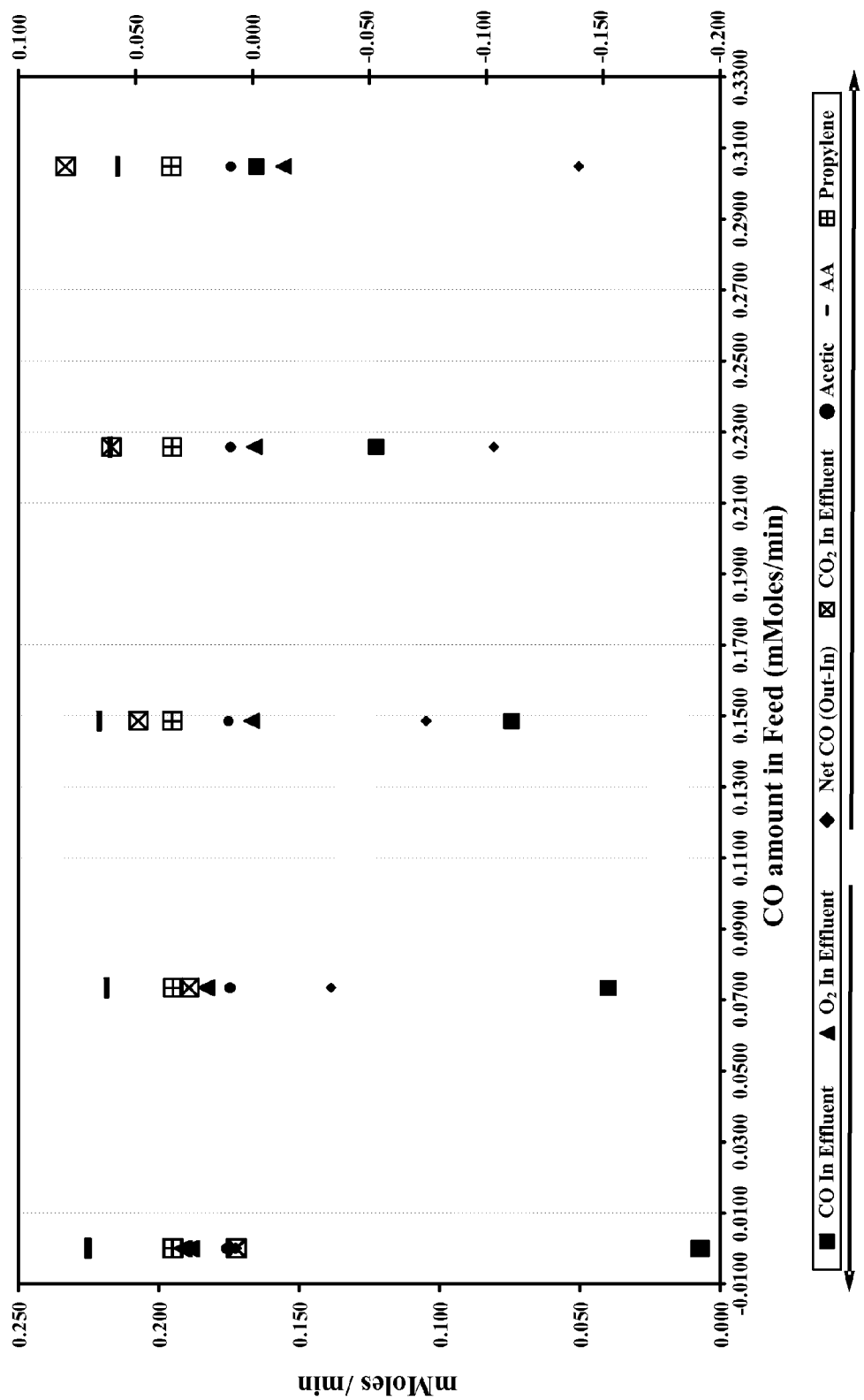
FIG. 16 depicts CO oxidation performance of Catalyst 7.
Figure 17:
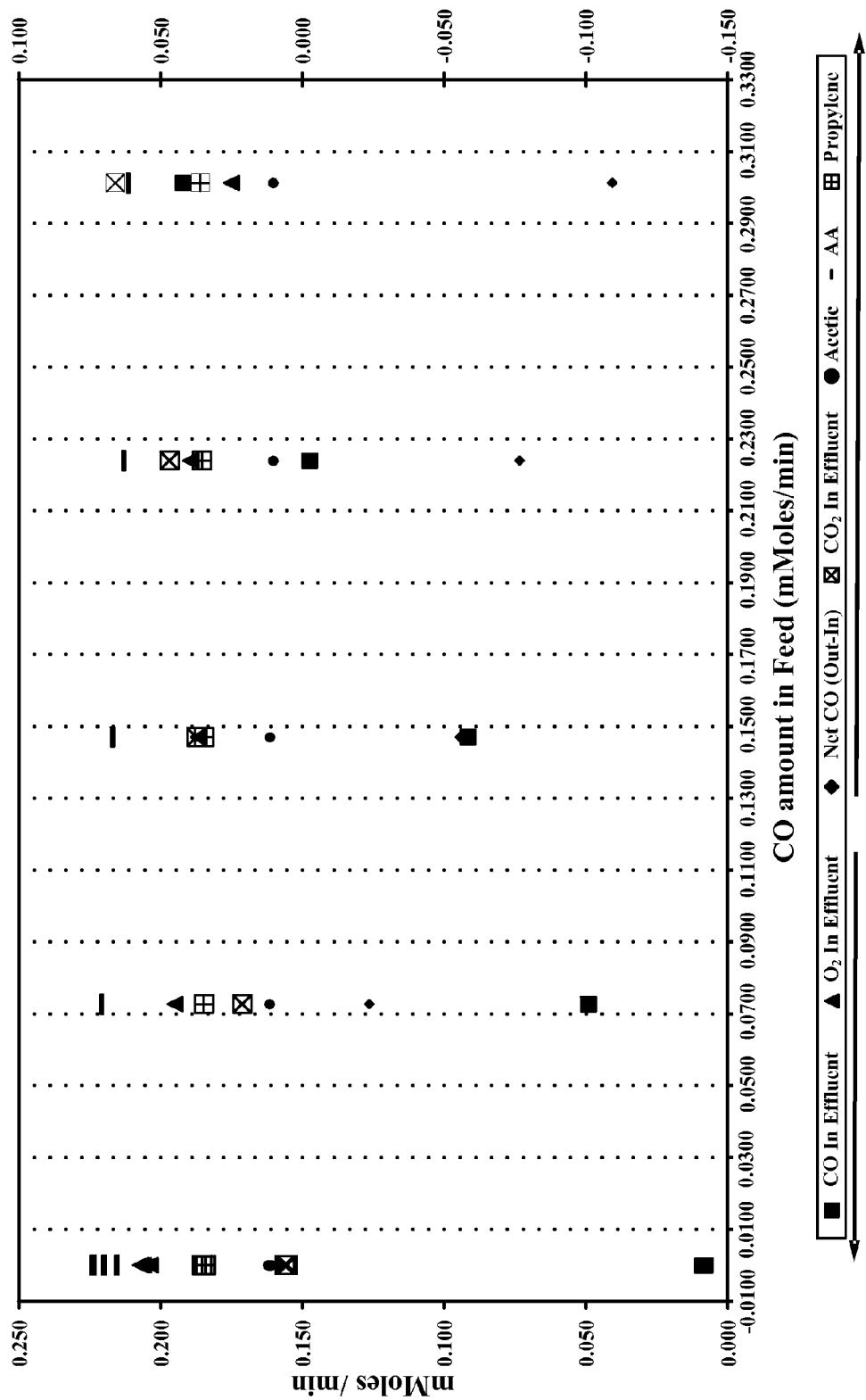
FIG. 17 depicts CO oxidation performance of Catalyst 8.

The ability of the platinum modified catalyst to co-oxidize CO was confirmed further by performing the CO oxidation test described in Table I for each of the platinum modified Catalyst 6, Catalyst 7, and Catalyst 8. The results of these CO oxidation tests are given in FIG. 15, FIG. 16, and FIG. 17, respectively. It can be concluded that when CO is present in the feed, CO is oxidized to $CO_2$ under propane oxidation conditions.

CLOSING PARAGRAPH OF THE INVENTION

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A composition comprising a compound of the following general formula (I):

$$MoV_aNb_bPt_cM_dZ_eO_x \qquad (I)$$

a is a number having a value of about 0.15 to about 0.50,
b is a number having a value of about 0.05 to about 0.30,
c is a number having a value of about 0.0001 to about 0.10,
d is a number having a value of greater than 0 to about 0.35,
e is a number having a value of 0 to about 0.10,
x is a number depending on the relative amount and valence of the elements different from oxygen in formula (I),
M is selected from the group consisting of Te; Te and Sb; Te and Ag; and Te, Ag, and Sb, if more than one M element is present, then each M element varies independently within the range of d, and Z is one or more element selected from the group consisting of Ru, Mn, Sc, Ti, Cr, Fe, Co, Ni, Cu, Zn, Ga, Y, Zr, Rh, Pd, In, Ce, Pr, Nd, Sm, Tb, Ta, W, Re, Ir, Au, Pb, and B, if more than one Z element is present, then each Z element varies independently within the range of e.

2. The composition of claim 1, wherein c is a number having a value between about 0.0001 and about 0.05.

3. The composition of claim 1, wherein c is a number having a value between about 0.0001 and about 0.03.

4. The composition of claim 1, wherein c is a number having a value between about 0.0001 and about 0.01.

5. The composition of claim 1, wherein the compound has platinum at a level of between about 0.1 wt. % to about 4.5 wt. %.

6. The composition of claim 5, wherein the compound has platinum at a level of between about 0.1 wt. % to about 1.2 wt. %.

7. The composition of claim 5, wherein the compound has platinum at a level of between about 0.1 wt. % to about 0.6 wt. %.

8. The composition of claim 5, wherein the compound has platinum at a level of between about 0.1 wt. % to about 0.3 wt. %.

9. A process for the conversion of a hydrocarbon to an unsaturated carboxylic acid comprising the steps of:
contacting a stream comprising a hydrocarbon having three to five carbon atoms, oxygen, and an inert component selected from the group consisting of nitrogen gas, steam, and mixtures thereof, in the presence of a composition comprising a compound of the following general formula (I):

$$MoV_aNb_bPt_cM_dZ_eO_x \quad (I)$$

a is a number having a value of about 0.15 to about 0.50,
b is a number having a value of about 0.05 to about 0.30,
c is a number having a value of about 0.0001 to about 0.10,
d is a number having a value greater than 0 to about 0.35,
e is a number having a value 0 to about 0.10,
x is a number depending on the relative amount and valence of the elements different from oxygen in formula (I), and
M is selected from the group consisting of Te; Te and Sb; Te and Ag; and Te, Ag, and Sb, if more than one M element is present, then each M element varies independently within the range of d;
Z is one or more or the following elements: Ru, Mn, Sc, Ti, Cr, Fe, Co, Ni, Cu, Zn, Ga, Y, Zr, Rh, Pd, In, Ce, Pr, Nd, Sm, Tb, Ta, W, Re, Ir, Au, Pb, B; if more than one Z element is present, then each Z element varies independently within the range of e;
forming an effluent stream from the contacting step; and
recovering the unsaturated carboxylic acid from the effluent stream.

10. The process of claim 9, further comprising recycling at least a portion of the effluent stream to said step of contacting.

11. The process of claim 10, wherein c is a number having a value between about 0.0001 and about 0.075.

12. The process of claim 10, wherein c is a number having a value between about 0.0001 and about 0.05.

13. The process of claim 10, wherein c is a number having a value between about 0.0001 and about 0.025.

14. The process of claim 10, wherein the compound has platinum at a level of between about 0.1 wt. % to about 4.5 wt. %.

15. The process of claim 10, wherein the compound has platinum at a level of between about 0.1 wt. % to about 1.2 wt. %.

16. The process of claim 10, wherein the compound has platinum at a level of between about 0.1 wt. % to about 0.6 wt. %.

17. The process of claim 10, wherein the compound has platinum at a level of between about 0.1 wt. % to about 0.3 wt. %.

18. The process of claim 10, wherein said hydrocarbon is one or more hydrocarbons having three carbon atoms, and said unsaturated carboxylic acid is acrylic acid.

19. A process of making a dual function oxidation catalyst capable of simultaneously oxidizing propane to acrylic acid and carbon monoxide to carbon dioxide comprising the steps of:
preparing a first aqueous solution including a molybdenum source, a vanadium source, a platinum source, and further includes a Te source; the Te source and an Sb source; the Te source and an Ag source; or the Te source, the Ag source, and the Sb source,
preparing a second aqueous solution including an organic acid and a niobium source,
adding the second aqueous solution to the first aqueous solution to form a catalyst precursor slurry,
drying the catalyst precursor, and
decomposing the catalyst precursor to form a catalyst composition,
where the platinum is present in an amount sufficient to form a catalyst having a weight percent of platinum between about 0.1 to about 4.5 based on the total weight of the catalyst;
wherein the catalyst composition is of the following general formula (I):

$$MoV_aNb_bPt_cM_dZ_eO_x \quad (I)$$

a is a number having a value of about 0.15 to about 0.50,
b is a number having a value of about 0.05 to about 0.30,
c is a number having a value of about 0.0001 to about 0.10,
d is a number having a value of greater than 0 to about 0.35,
e is a number having a value of 0 to about 0.10,
x is a number depending on the relative amount and valence of the elements different from oxygen in formula (I),
M is selected from the group consisting of Te; Te and Sb; Te and Ag; and Te, Ag, and Sb, if more than one M element is present, then each M element varies independently within the range of d, and
Z is one or more element selected from the group consisting of Ru, Mn, Sc, Ti, Cr, Fe, Co, Ni, Cu, Zn, Ga, Y, Zr, Rh, Pd, In, Ce, Pr, Nd, Sm, Tb, Ta, W, Re, Ir, Au, Pb, and B, if more than one Z element is present, then each Z element varies independently within the range of e.

20. The process of claim 19, wherein the first aqueous solution further includes a source of one or more metals selected from the group consisting of Ru, Mn, Sc, Ti, Cr, Fe, Co, Ni, Cu, Zn, Ga, Y, Zr, Rh, Pd, In, Ce, Pr, Nd, Sm, Tb, Ta, W, Re, Ir, Au, Pb, and B.

21. The process of claim 19, wherein the drying is in air at 120° C. for 1 hr, and the decomposing is at 300° C. for 5 hrs.

22. The process of claim 19, further comprising the step of: calcining the catalyst precursor in argon at 600° C. for 2 hrs.

23. The process of claim 19, further comprising the steps:
prior to the adding step, heating the first aqueous solution at a first temperature and for a first time to dissolve the sources, and cooling the heated first aqueous solution, and
prior to the adding step, heating the second aqueous solution at a second temperature and for a second time to dissolve the sources, and cooling the heated second aqueous solution.

24. The process of claim 23, wherein the first temperature is 90° C. and the first time is 1 hour and the first aqueous solution is cooled to 35° C. and the second temperature is between 95° C. and 100° C. and the second time is 1 hour.

25. The composition of claim 1 wherein the compound has the following general formula:

$$MoV_aNb_bPt_cSb_{d1}Te_{d2}Z_eO_x$$

d1 is a number having a value of greater than 0 to about 0.30, and d2 is a number having a value between about 0.01 and about 0.30.

26. A composition consisting of a compound of the following general formula (I):

$$MoV_aNb_bPt_cM_dZ_eO_x \quad (I)$$

a is a number having a value of about 0.15 to about 0.50,
b is a number having a value of about 0.05 to about 0.30,
c is a number having a value of about 0.0001 to about 0.10,
d is a number having a value of greater than 0 to about 0.35,
e is a number having a value of 0 to about 0.10,
x is a number depending on the relative amount and valence of the elements different from oxygen in formula (I),
M is selected from the group consisting of Te; Te and Sb; Te and Ag; and Te, Ag, and Sb, if more than one M element is present, then each M element varies independently within the range of d, and
Z is one or more element selected from the group consisting of Ru, Mn, Sc, Ti, Cr, Fe, Co, Ni, Cu, Zn, Ga, Y, Zr, Rh, Pd, In, Ce, Pr, Nd, Sm, Tb, Ta, W, Re, Ir, Pb, and B, if more than one Z element is present, then each Z element varies independently within the range of e.

* * * * *